United States Patent
Woscholski et al.

(10) Patent No.: US 7,692,012 B2
(45) Date of Patent: Apr. 6, 2010

(54) VANADIUM COMPOUNDS AS INHIBITORS OF PHOSPHATASES

(75) Inventors: Rudiger Woscholski, London (GB); Erika Rosivatz, London (GB); Ramon Vilar, London (GB)

(73) Assignee: Imperial College Innovations Limited, London (GB)

( * ) Notice: Subject to any disclaimer, the term of this patent is extended or adjusted under 35 U.S.C. 154(b) by 635 days.

(21) Appl. No.: 10/581,000

(22) PCT Filed: Dec. 6, 2004

(86) PCT No.: PCT/GB2004/005080

§ 371 (c)(1),
(2), (4) Date: May 10, 2007

(87) PCT Pub. No.: WO2005/054257

PCT Pub. Date: Jun. 16, 2005

(65) Prior Publication Data

US 2007/0292532 A1    Dec. 20, 2007

(30) Foreign Application Priority Data

Dec. 4, 2003 (GB) ................................. 0328157.3

(51) Int. Cl.
*C07F 9/00* (2006.01)
*A61K 33/26* (2006.01)

(52) U.S. Cl. .................... 546/10; 556/42; 514/492; 546/2; 424/646

(58) Field of Classification Search ............... 424/646; 514/492; 546/2, 10; 556/42
See application file for complete search history.

(56) References Cited

U.S. PATENT DOCUMENTS

2003/0055106 A1   3/2003   Faure et al.

FOREIGN PATENT DOCUMENTS

| GB | 2 396 106 A | 6/2004 |
| WO | 00/57860 A2 | 10/2000 |
| WO | 2004/018655 A2 | 3/2004 |

OTHER PUBLICATIONS

M. Zhao, British Journal of Pharmacology, vol. 152, pp. 1141-1144 (2007).*
Julius A. Gordon, Methods in Enzymology, vol. 201, pp. 477-482 (1991).*
Schmid, Annette C., et al., "Bisperoxovanadium compounds are potent PTEN inhibitors," FEBS Letters, 566: 35-38 (2004).
Nolte, Lorraine A., et al., "A peroxovanadium compound stimulates muscle glucose transport as powerfully as insulin and contractions combined," Diabetes, 52(8): 1918-1925 (2003).

(Continued)

Primary Examiner—Porfirio Nazario Gonzalez
(74) Attorney, Agent, or Firm—Elmore Patent Law Group, P.C.; Carolyn S. Elmore; Mahreen Chaudhry Hoda

(57) ABSTRACT

Novel Vanadium compounds are described as well as their use as inhibitors of phosphatases, particularly inositol phosphatases, The use of the compound in the treatment of nerodegenerative diseases is also described.

15 Claims, 10 Drawing Sheets

$IC_{50}$ values

Figure 2A:
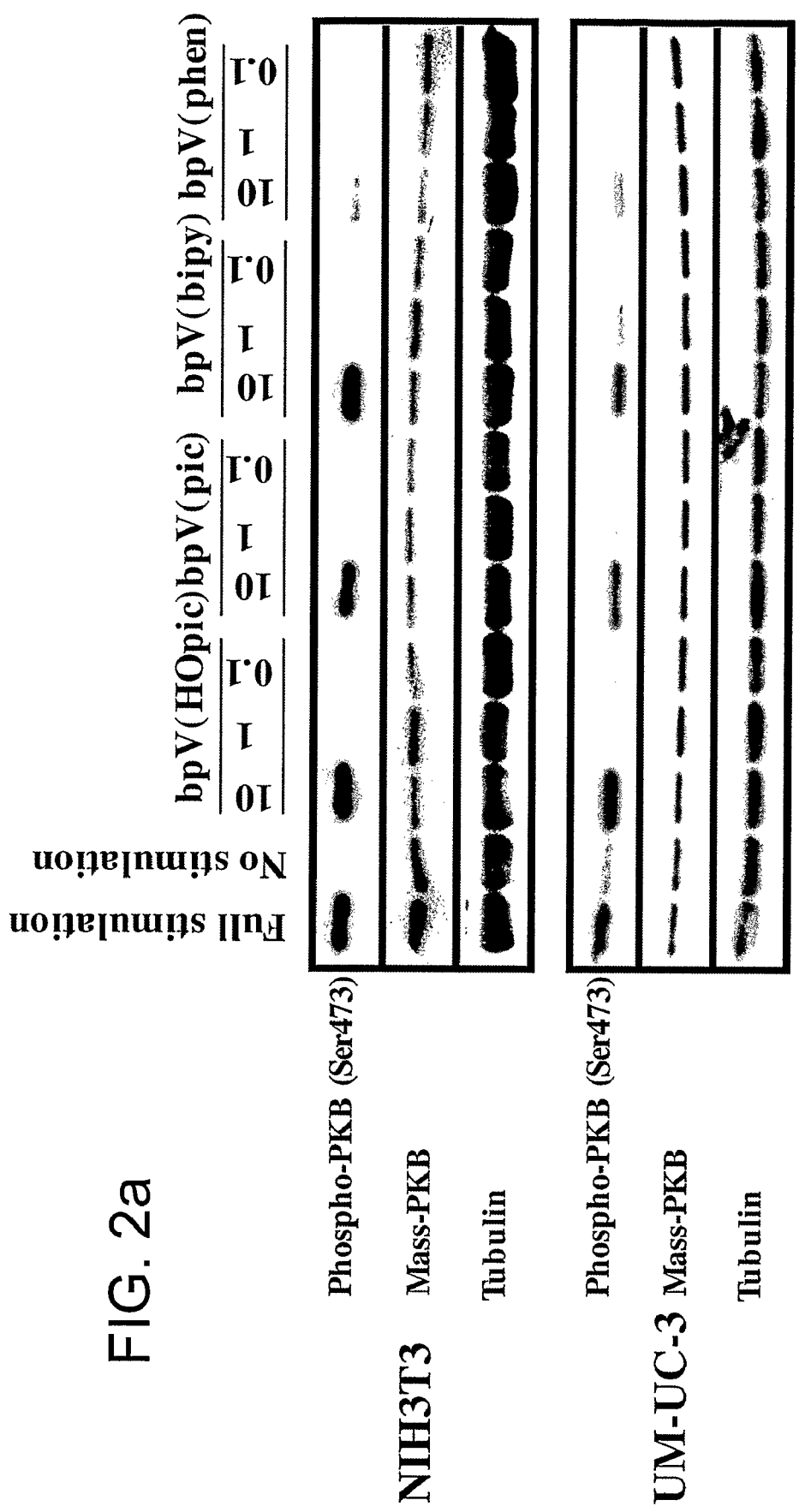

| enzyme \ inhibitor | Aromatic bpVs | | Polar bpVs | |
|---|---|---|---|---|
| | bpV (bipy) | bpV (phen) | bpV (HOpic) | bpV (pic) |
| PTP-β | 60.3 nM +/- 9.6 | 343 nM +/- 88.5 | 4.9 μM +/- 0.9 | 12.7 μM +/- 3.2 |
| PTP-1B | 164 nM +/- 22.6 | 920 nM +/- 45.2 | 25.3 μM +/- 2.9 | 61 μM +/- 10.5 |
| PTEN | 18 nM +/- 0.8 | 38 nM +/- 2.4 | 14 nM +/- 2.3 | 31 nM +/- 1.7 |

OTHER PUBLICATIONS

Band, Christian J., et al., "Early signaling events triggered by peroxovanadium [bpV(phen)] are insulin receptor kinase (IRK)-dependent: specificity of inhibition of IRK-associated protein tyrosine phosphatase(s) by bpV(phen)," Molecular Endocrinology, 11(13): 1889-1910 (1997).

Band, Christian J. and Posner, Barry I., "Phosphatidylinositol 3'-Kinase and p70s6k are Required for Insulin but not Bisperoxovanadium 1, 10-phenanthroline (bpv(phen)) Inhibition of Insulin-like Growth Factor Binding Protein Gene Expression," J. Biological Chemistry, 272(1): 138-145 (1997).

Barat, Corrine and Tremblay, Michael J., "Treatment of Human T Cells with Bisperoxovanadium Phosphotyrosyl Phosphatase Inhibitors Leads to Activation of Cyclooxygenase-2 Gene," J. Biological Chemistry, 278(9): 6992-7000 (2002).

Sasagawa, Takahiro, et al., "Bis(6-ethylpicolinato)oxovanadium(IV) Complex with Normoglycemic Activity in KK-Ay Mice," J. Inorganic Biochemistry, 88(1): 108-112 (2002).

Kozlov, Alexander, et al., "Zeolite-encapsulated vanadium picolinate peroxo complexes active for catalytic hydrocarbon oxidations," J. Molecular Catalysis A: Chemical, 137: 223-237 (1999).

Posner, B.I., et al., Peroxovanadium Compounds. A New Class of Potent Phosphotyrosine Phosphatase Inhibitors Which are Insulin Mimetics, J. Biol. Chem., 269 (6): 4596-4604 (1994).

Cuncic, C., et al., "Vanadate Inhibition of Protein Tyrosine Phosphatases in Jurkat Cells: Modulation by Redox State," J. Biol. Inorg. Chem., 4: 354-359 (1999).

Huyer, G., et al., "Mechanism of Inhibition of Protein-Tyrosine Phosphatases by Vanadate and Pervanadate," J. Biol. Chem., 272(2): 843-851 (1997).

Rumora, L., et al., "Differential Regulation of JNK Activation and MKP-1 Expression by Peroxovanadium Complexes," Neurochem. Int., 38: 341-347 (2001).

Shisheva, A. and Shechter, Y., et al., "Mechanism of Pervanadate Stimulation and Potentiation of Insulin-Activated Glucose Transport in Rat Adipocytes: Dissociation from Vanadate Effect," Endocrinology, 133(4): 1562-1568 (1993).

Wilden, P.A.. and Broadway, D., "Combination of Insulinomimetic Agents H2O2 and Vanadate Enhances Insulin Receptor Mediated Tyrosine Phosphorylation of IRS-1 Leading to IRS-1 Association with the Phosphatidylinositol 3-kinase," J. Cell Biochem., 58: 279-291 (1995).

Shechter, Y., "Insulin-Mimetic Effects of Vanadate. Possible Implications for Future Treatment of Diabetes," Diabetes, 39: 1-5 (1990).

Stephens, L.R., et al., "Agonist-Stimulated Synthesis of Phosphatidylinositol(3,4,5)-Trisphosphate: A New Intracellular Signalling System?" Biochim. et Biophys. Acta, 1179: 27-75 (1993).

* cited by examiner

FIG. 1 IC$_{50}$ values

| enzyme \ inhibitor | Aromatic bpVs | | Polar bpVs | |
| --- | --- | --- | --- | --- |
| | bpV (bipy) | bpV (phen) | bpV (HOpic) | bpV (pic) |
| PTP-β | 60.3 nM +/- 9.6 | 343 nM +/- 88.5 | 4.9 μM +/- 0.9 | 12.7 μM +/- 3.2 |
| PTP-1B | 164 nM +/- 22.6 | 920 nM +/- 45.2 | 25.3 μM +/- 2.9 | 61 μM +/- 10.5 |
| PTEN | 18 nM +/- 0.8 | 38 nM +/- 2.4 | 14 nM +/- 2.3 | 31 nM +/- 1.7 |

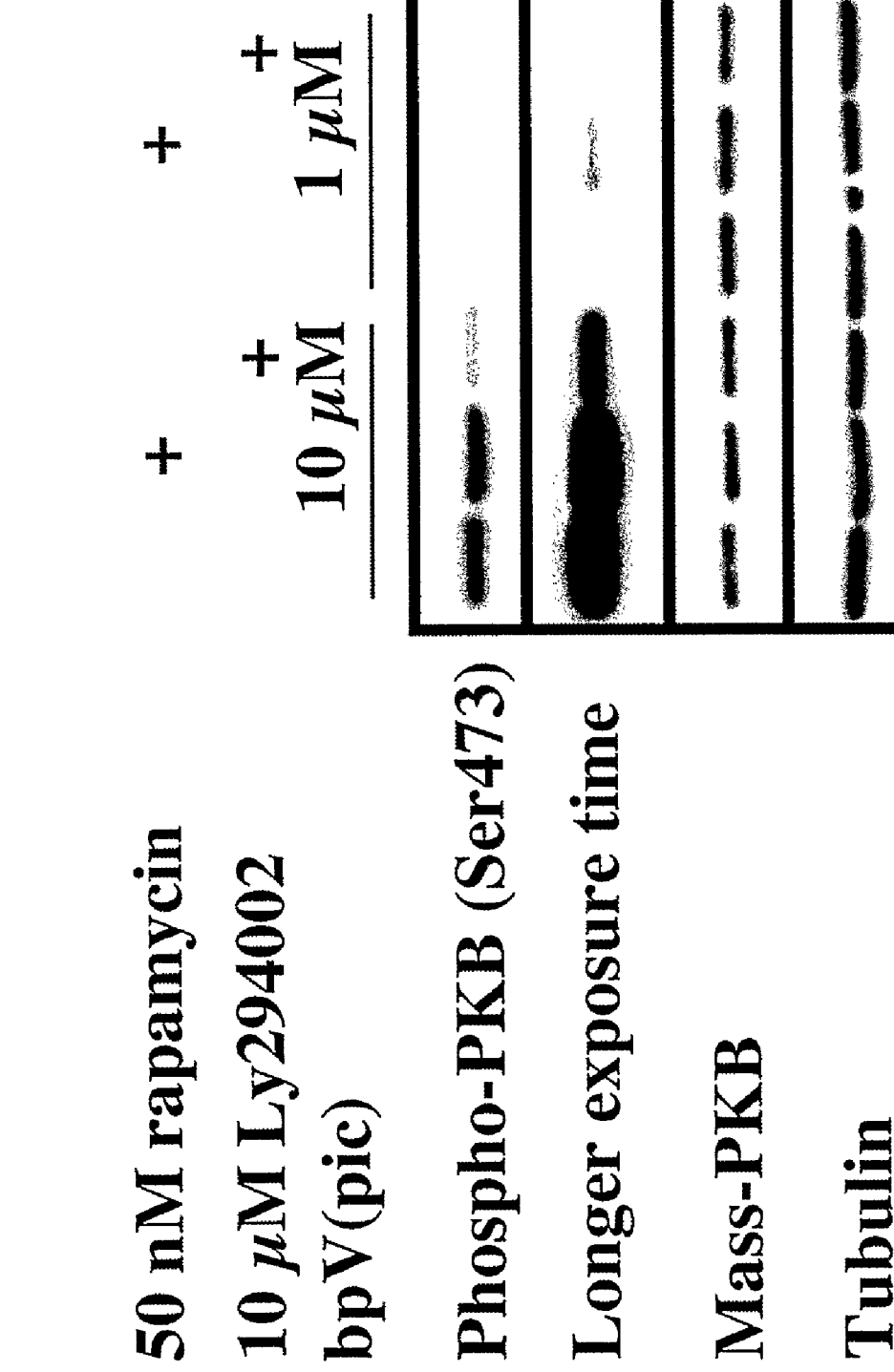

FIG. 7

| property \ inhibitor class | polar inhibitors | aromatic inhibitors |
|---|---|---|
| Cytotoxicity MTT | high μmolar | high μmolar |
| Cytotoxicity actin | μmolar | μmolar |
| Insulin mimetic pSer473(PKB) | μmolar | μmolar |
| Insulin mimetic pTyr | μmolar | μmolar |
| PTP inhibition *in vitro* | high nanomolar | μmolar |
| PTEN inhibition *in vitro* | low nanomolar | low nanomolar |
| PTEN inhibition *in vivo* | nanomolar | nanomolar |
| Inhibitor sensitivity rapamycin (PKB) | stimulates phosphorylation | |
| Inhibitor sensitivity Ly294002 (pTyr) | inhibits phosphorylation | |

VANADIUM COMPOUNDS AS INHIBITORS OF PHOSPHATASES

The present invention relates to novel compounds and their use in the inhibition of phosphatases, particularly inositol phosphatases. The compounds thus find use in treating neurodegenerative diseases as well as other conditions where inhibition of apoptosis would be benficial.

Vanadate, peroxovanadium (pV) and bisperoxovanadium (bpV) derivates are well known inhibitors of protein tyrosine phosphatases (PTPases) whereby bpVs are more potent than the other two molecule classes [Posner, 1994 #157] [Cuncic, 1999 #221]. Vanadate, a phosphate analogue, is a competitive inhibitor of PTP-1B while pervanadate irreversibly oxidizes the catalytic cysteine of PTP-1B [Huyer, 1997 #220]. Peroxovanadium compounds which show higher stability than pervanadates have been recently synthesised [Posner, 1994 #157]. Beside other biological functions they all exhibit insulin mimetic features [Rumora, 2001 #153], e. g. increase of glucose transport in adipocytes [Shisheva, 1993 #260], enhancement of insulin receptor-mediated tyrosine phosphorylation of insulin receptor substrate (IRS)-1 [Wilden, 1995 #259] and induction of insulin receptor kinase (IRK) phosphorylation by inhibiting IRK-associated PTPases [Band, 1997 #155].

The insulin mimetic downstream effect is thought to be mainly originated by the inhibition of PTPases that are involved in dephosphorylating the insulin receptor resulting in a prolonged insulin signal [Shechter, 1990 #258]. All PTPases share the same active site the so-called CX5R motif. This sequence homology has been also found in some phosphoinositol phosphatases such as the SAC phosphatase, Myotubularin (MTM) and PTEN (phosphatase and tensin homologue deleted on chromosome 10) (for review: see No 98). The latter was originally thought to be a PTPase but has subsequently been shown to possess higher affinity towards 3-phosphorylated phosphoinositides (PI) such as PI(3)P, PI(3,4,5)P3 and I(3,4,5)P4 [Maehama, 1998 #175].

PTEN is a tumour suppressor which in many cancer cells is either mutated or deleted [Li, 1997 #255] [Steck, 1997 #256] [Waite, 2002 #262] (No 289). 3-phosphorylated lipids are mainly generated by the phosphoinositol 3 kinase (PI3K) in response to an extracellular stimulation. By dephosphorylating intracellular PI(3,4,5)P3 PTEN counteracts the PI3K and therefore inhibits the protein kinase B (PKB) activity (No 232, No 236, No 265) one of the main downstream targets of PI3K. PKB also referred to Akt [Downward, 1998 #254] is the mammalian homologue of the viral oncoprotein v-akt (No 284). Since PI(3,4,5)P3 is an important second messenger involved i. e. in cell growth signalling, [Stephens, 1993 #257] one can say that PTEN terminates important signalling pathways in the cell leading to apoptosis (No 202).

In addition, PTEN has been shown to block cell cycle progression by negative regulation of the PI3K/PKB pathway (No 235) and is involved in the regulation of angiogenesis (No 191). The loss of PTEN in malignant melanoma led to the activation of PKB (No 275). Stocker et al [Stocker, 2002 #186] have recently shown that in a Drosophila mutant lacking PTEN increased levels of PI(3,4,5)P3 directly effect PKB. PI(3,4,5)P3 binds to a N-terminal pleckstrin homology (PH) domain of PKB and subsequently leads to conformational changes (No 287) and its recruitment to the membrane. Upon translocation PKB is phosphorylated at two major sites (Thr308 and Ser473) which is crucial for its activity (No 285). Threonine is phosphorylated by the phosphoinositol dependent kinase-1 (PDK-1) (No 286) which in turn is activated by PI(3,4,5)P3 binding to their PH domains (for review see: [Downward, 1998 #254] [Hill, 2002 #237]). The kinase which phosphorylates the serine residue remains unknown.

We have now found that certain Vanadium based compounds represent a new class of PTEN inhibitors, the bpV compounds. These inhibitors show significant lower $IC_{50}$ values for PTEN as demonstrated for PTPases, in vitro and in vivo. Thus, the use of these molecules allows the distinction between different groups of phosphatases.

Thus, in a first aspect, the present invention provides the use of a Vanadium containing compound of the formula:

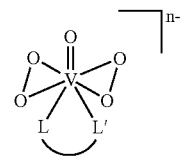

wherein L-L' is:

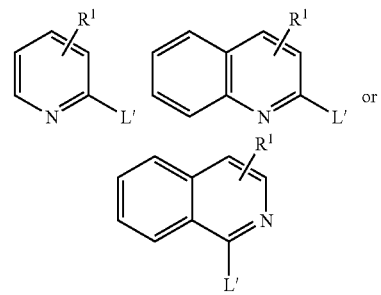

and L' is $COO$, $CONR^5$, $CONHR^6$, $CH_2NR^5R^6$ or wherein L and L' together form a group:

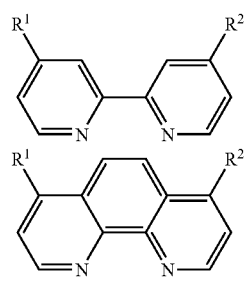

or a group:

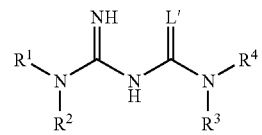

wherein L" is O, S or NH;

$R^1$, $R^2$, $R^3$, $R^4$, $R^5$ and $R^6$ are independently H, hydroxyl, $C_{1-6}$ alkyl, optionally substituted by hydroxy or $NR^7R^8$, $C_{3-6}$ cycloalkyl, optionally substituted by hydroxy or $NR^7R^8$, phenyl, optionally substituted by $C_{1-3}$ alkyl, hydroxy, $NR^7R^8$ or $SO_3$, $(OCH_2CH_2)_n(NHCH_2CH_2)_n$, an amino acid or a peptide consisting of 2 to 5 amino acids; and $R^7$ and $R^8$ are independently H or $C_{1-6}$ alkyl;

or a pharmaceutically acceptable salt thereof in the manufacture of a medicament for use in inhibiting phosphatases.

In a second aspect the present invention provides a Vanadium containing compound of the formula:

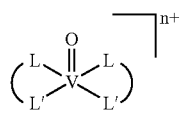

wherein L-L' is:

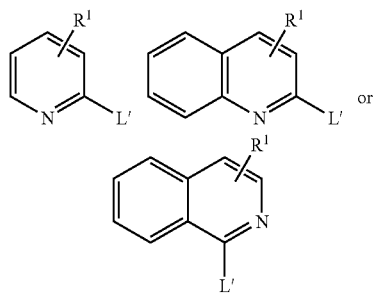

and L' is COO, $CONR^5$, $CONHR^6$, $CH_2NR^5R^6$ or wherein L and L' together form a group:

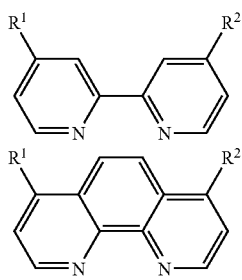

or a group:

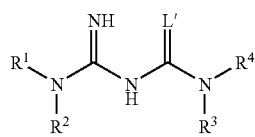

wherein L" is O, S or NH;

$R^1, R^2, R^3, R^4, R^5$ and $R^6$ are independently H, hydroxyl, $C_{1-6}$ alkyl, optionally substituted by hydroxy or $NR^7R^8$, $C_{3-6}$ cycloalkyl, optionally substituted by hydroxy or $NR^7R^8$, phenyl, optionally substituted by $C_{1-3}$ alkyl, hydroxy, $NR^7R^8$ or $SO_3$, $(OCH_2CH_2)_n(NHCH_2CH_2)_n$, an amino acid or a peptide consisting of 2 to 5 amino acids; and $R^7$ and $R^8$ are independently H or $C_{1-6}$ alkyl;

or a pharmaceutically acceptable salt thereof in the manufacture of a medicament for use in inhibiting phosphatases.

Preferred compounds for use in the invention include potassium bisperoxo (bipyridine) oxovanadate (bpV(bipy), potassium bisperoxo(1,10-phenanthroline)oxovanadate (pV (phenanthroline)), potassium bisperoxo (piconlinate) oxovanadate (pV(pic)) and potassium bisperoxo(phenylbiguanide)oxovanadate (pV(biguan)).

In particular two compounds, pV(phenbig) [dipotassium bisperoxo(phenylbiguanide)oxovanadate] or bpV(HOpic) [dipotassium bisperoxo(5-hydroxypyridine-2-carboxyl)oxovanadate], have been found to specifically inhibit PTEN, but not SopB, MTM or PTP. As such these compounds would be particularly useful in the treatment of diabetes.

The peroxovanadates derived from the $R^1R^2N$—$C(=NH)$—$NH$—$C(=E)$-$NR^3R^4$, (E=NH, S, O) ligands are novel compounds and represent independent aspects of the invention. Similarly, the peroxovanadates derived from the 2-piconilamide ligands (whether they are N,N or N,O coordinated) are also novel representing independent aspects of the invention.

As discussed herein, the compounds described herein find use as inhibitors of phosphatases, in particular PTEN. As such, therefore, they find use as treatments of nurodegenerative disease such as Alzheimer's disease as well as diseases or conditions which benefit from inhibition of apoptosis, such as wound healing, burns, heart hypertrophy, hypoxia, ischemia, diabetes and sports injuries. In addition, cancer cells are more resistant to apoptosis and thus the compounds of the invention would find use in combination with conventional chemotherapy agents as protecting normal cells, which are more likely to undergo apoptosis.

The medicaments as described herein may be presented in unit dose forms containing a predetermined amount of each active ingredient per dose. Such a unit may be adapted to provide 5-100 mg/day of the compound, preferably either 5-15 mg/day, 10-30 mg/day, 25-50 mg/day 40-80 mg/day or 60-100 mg/day. For compounds of formula I, doses in the range 100-1000 mg/day are provided, preferably either 100-400 mg/day, 300-600 mg/day or 500-1000 mg/day. Such doses can be provided in a single dose or as a number of discrete doses. The ultimate dose will of course depend on the condition being treated, the route of administration and the age, weight and condition of the patient and will be at the doctor's discretion.

The compounds described herein are most preferably administered in the form of appropriate compositions. As appropriate compositions there may be cited all compositions usually employed for systemically or locally administering drugs. The pharmaceutically acceptable carrier should be substantially inert, so as not to act with the active component. Suitable inert carriers include water, alcohol, polyethylene glycol, mineral oil or petroleum gel, propylene glycol and the like. Said pharmaceutical preparations may be formulated for administration in any convenient way for use in human or veterinary medicine.

As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. However, in certain embodiments the subject agents may be simply dissolved or suspended in sterile water. In certain embodiments, the pharmaceutical preparation is non-pyrogenic, i.e., does not elevate the body temperature of a patient. The phrase "effective amount" as used herein means that amount of one or more agent, material, or composition comprising one or more agents of the present invention which is effective for producing some desired effect in an animal. It is recognized that when an agent is being used to achieve a therapeutic effect, the actual dose which comprises the "effective amount" will vary depending on a number of conditions including the particular condition being treated, the severity of the disease, the size and health of the patient, the route of administration, etc. A skilled medical practitioner can readily determine the appropriate dose using methods well known in the medical arts. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such asethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, one or more agents may contain a basic functional group, such as amino or alkylamino, and are, thus, capable of forming pharmaceutically acceptable salts with pharmaceutically acceptable acids.

The term "pharmaceutically acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the ydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (Berge, Bighley et al. 1977). The pharmaceutically acceptable salts of the agents include the conventional non-toxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2acetoxybenzoic, fumaric, toluenesulfonic, methanesulfonic, ethane disulfonic, oxalic, isothionic, and the like. In other cases, the one or more agents may contain one or more acidic functional groups and, thus, are capable of forming pharmaceutically acceptable salts with pharmaceutically acceptable bases. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine.

Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (see, for example, Berge et al., supra) Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like. Formulations of the present invention include those suitable for oral, nasal, topical (including buccal and ublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred per cent, this amount will range from about 1 percent to about ninety-nine percent of active ingredient, preferably from bout 5 percent to about 70 percent, most preferably from about 10 percent to about 30 percent. Methods of preparing these formulations or compositions include the step of bringing into association an agent with the carrier and, optionally, one or more accessory ingredients. In general, the formulations are prepared by uniformly and intimately bringing into association an agent of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste. In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, olyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like. A tablet may be made by compression or molding, optionally with one or more accessory ingredients. Compressed tablets may be repaired using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes.

The active ingredient can also be in micro-encapsulated form, if appropriate, with one or more of the above-described excipients. Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol. polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents. Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the agents. Formulations of the present invention which are suitable for vaginal administration also include pessaries, tampons, creams, gels, pastes, foams or spray formulations containing such carriers as are known in the art to be appropriate. Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane. Transdermal patches have the added advantage of providing controlled delivery of a compound of the present invention to the body. Such dosage forms can be made by dissolving or dispersing the agents in the proper medium.

Absorption enhancers can also be used to increase the flux of the agents across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin. In some cases, in order to prolong the effect of an agent, it is desirable to slow the absorption of the agent from subcutaneous or intramuscular injection. This may be accomplished by the use of a liquid suspension of crystalline or amorphous material having poor water solubility. The rate of absorption of the agent then depends upon its rate of dissolution which, in turn, may depend upon crystal size and crystalline form. Alternatively, delayed absorption of a parenterally administered agent form is accomplished by dissolving or suspending the agent in an oil vehicle. Injectable depot forms are made by forming microencapsule matrices of the subject compounds in biodegradable polymers such as polylactide-polyglycolide. Depending on the ratio of agent to polymer, and the nature of the particular polymer employed, the rate of agent release can be controlled. Examples of other biodegradable polymers include poly(orthoesters) and poly(anhydrides). Depot injectable formulations are also prepared by entrapping the agent in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier. Apart from the above-described compositions, use may be made of covers, e.g., plasters, bandages, dressings, gauze pads and the like, containing an appropriate amount of a therapeutic. As described in detail above, therapeutic compositions may be administered/delivered on stents, devices, prosthetics, and implants.

Compounds as described herein can be synthesised according to the following general procedures:

Synthesis of Peroxovanadates with General Formula: $[M]_n[V(=O)(O_2)_2(L-L)]$ (where M=Na, K or $NH_4$)

In a typical procedure $K_2[V(=O)(O_2)_2(pic)].H_2O$ (pic=pyridine-2-caroxylate) was prepared by adding distilled water to $V_2O_5$ (0.69 g, 3.8 mmol) and KOH (0.49 g, 8.8 mmol) to form a yellow-brown suspension. This was followed by addition of $H_2O_2$ (0.5 ml of a 30% w/v) which produced a bright orange solution with some brown precipitate. The brightly colored solution was filtered through a sinter glass filter and allowed to stand for 30 minutes. More $H_2O_2$ (10 ml) was added to the reaction mixture followed by addition of picolinic acid (0.97 g, 7.9 mmol). The solution was stirred for further 30 minutes after which time ethanol (40 ml) was added dropwise precipitating a bright yellow compound. This solution was left standing at 4° C. for two days and all yellow solid produced was collected by filtration, washed 3 times with dry ethanol and dried under reduced pressure overnight (yields vary between 40 and 80% depending on the L-L ligand used). The pV complexes can be characterized by infrared, uv visible, $^1H$ NMR and $^{51}V$ NMR spectroscopy. Elemental analyses can be used to confirm the purity of the samples.

This synthetic procedure is based in previously reported ones:

[1] Alan Shaver, Jesse B. Ng. David A. Hall, Bernadette Soo Lum, and Barry I. Posner, *Inorg. Chem.* 1993, 32, 3109-3113

[2] Barry I. Posner, Robert Faureb, James W. Burgess, A. Paul Bevand, Danielle Lachance, Guiyi Zhang-Sun, I. George Fantus, Jesse B. Ng, David A. Hall, Bernadette Soo Lum and Alan Shavers, *J. Biol. Chem.* 1994, 269, 4596-4604

Synthesis of Vanadates with General Formula: $[V(=O)(L-L)_2]$ and $[M]_2[V(=O)(L-L)_2]$ (M=Na, K, $NH_4$)

In a typical procedure $[V(=O)(pic)_2].H_2O$ was prepared by adding a solution of picolinic acid (0.83 g, 6.5 mmol) in water (20 mL) to $[V(=O)(SO_4)].3H_2O$ (0.72 g, 3.30 mmol) in water (20 mL). The pH was raised to 4.4 with dropwise additions of 2 M NaOH. The light blue solid which precipitated was isolated by filtration and washed with methanol and diethyl ether several times. The solid was dried under reduced pressure (yields vary between 45 and 90% depending on the L-L ligand used). The vanadate complexes can be characterized by infrared and uv visible spectroscopy, mass spectrometry and magnetic momentum determination. Elemental analyses can be used to confirm the purity of the samples.

This synthetic procedure is based in previously reported ones:

[1] Marco Melchior, Katherine H. Thompson, Janet M. Jong, Steven J. Rettig, Ed Shuter,
Violet G. Yuen, Ying Zhou, John H. McNeill, and Chris Orvig, *Inorg. Chem.* 1999, 38, 2288-2293

In a third aspect, the present invention provides a method of inhibiting a phosphatase which comprises administering to a subject an effective amount of a compound as described herein. In particular, the phosphatase is PTEN and more particularly, the invention provides a method of treating a neurodegenerative disease such as Alzheimer's disease as well as diseases or conditions which benefit from inhibition of apoptosis, such as wound healing, burns, heart hypertrophy, hypoxia, ischemia and sports injuries. In addition, cancer cells are more resistant to apoptosis and thus the compounds of the invention would find use in combination with conventional chemotherapy agents as protecting normal cells, which are more likely to undergo apoptosis.

The invention will now be described with reference to the following examples, which should not in any way be construed as limiting the invention:

The examples refer to the figures in which:

FIG. 1: shows $IC_{50}$ values for bpV compounds (bpV(bipy), bpV(phen), bpV(HOpic), and bpV(pic)) for the protein tyrosine phosphatases PTP-β and PTP-1B and the phosphoinositol 3-phosphatase PTEN. Experiments for PTPases were performed using pNPP as a substrate and concentrations of inhibitors between 100 μM and 1 nM. One can distinguish a significant difference between the two groups of inhibitors. Aromatic bpVs showed higher nanomolar $IC_{50}$, however μmolar concentrations were needed to inhibit PTPs by polar bpV compounds. Studies for PTEN were accomplished with a malachite green based phosphate release assay. We used PI(3,4,5)P3 as a substrate and measured released phosphate without and in the presence of bpV inhibitors at concentrations ranging from 0.1 to 500 nM. These PTP inhibitors could be established as very potent PTEN inhibitors showing 50% inhibition at low nanomolar concentrations. All $IC_{50}$ values were presented as the means+/−S.E. of triplicate determinations. Calculations were performed using Prism GraphPad.

FIG. 2a Insulin mimetic property of bpV compounds: NIH3T3 and UM-UC-3 cells starved for 72 h were incubated for 15 min with concentrations between 10 μM and 0.1 μM of all four bpV inhibitors. Cell lysates were analysed by SDS-PAGE and subsequent Western blotting using pSer473 PKB, Mass PKB and tubulin antibodies. The highest concentration (10 μM) showed for all four bpVs phosphorylation of PKB indicating the induction of the insulin pathways. 1 μM and 0.1 μM did only effect slight phosphorylation or none. bpV(phen) was revealed as being less potent in terms of insulin mimetic property, showing lower phosphorylation of PKB compared to the other compounds. The panel shows results from an experiment representative of three others.

Figure 2B:
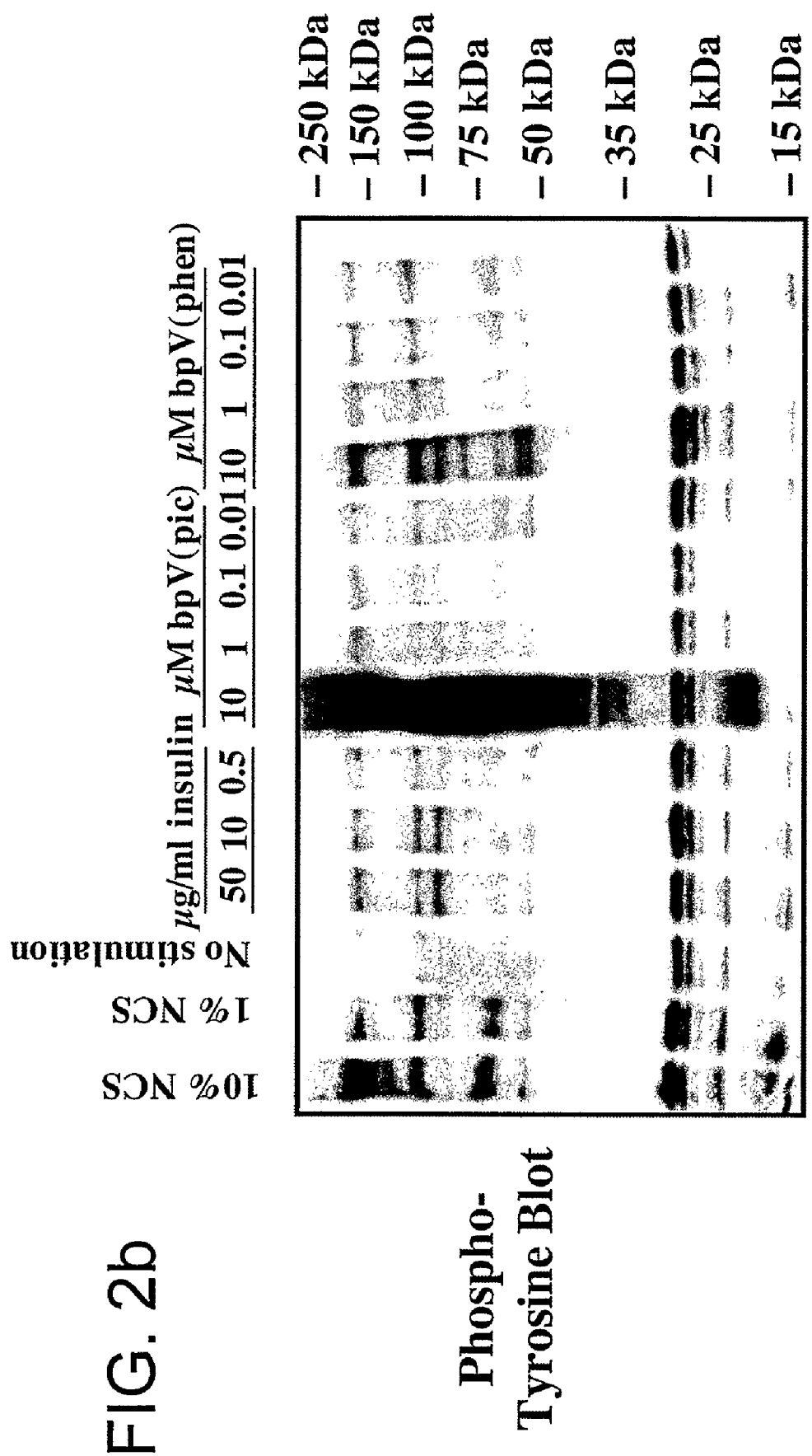

FIG. 2b Phosphorylation of tyrosine residues induced by growth factors, bpV(pic) and bpV(phen): Quiescent NIH3T3 cells were exposed to 10% NCS, 50, 10 and 0.5 μg/ml insulin and various concentrations of bpV(pic) and bpV(phen), for 15 min. The Western Blot analyses with specific antiphosphotyrosine antibody demonstrated the expected protein band pattern which gave highest phosphorylation signals for 10 μM bpV(pic). In comparison, 10 μM bpV(phen) induced lower phosphorylation rate, whereas similar to fibroblast stimulated with 10%. Concentrations at the nmolar range had no implication on phosphorylation of tyrosine residues. Co-stimulation of cells with 0.01 μM bpV and 0.5 μg/ml insulin did not result altered phosphorylation when compared to control cells. Molecular size is indicated on the right. The figure shows a representative blot out of three others.

Figure 2C:
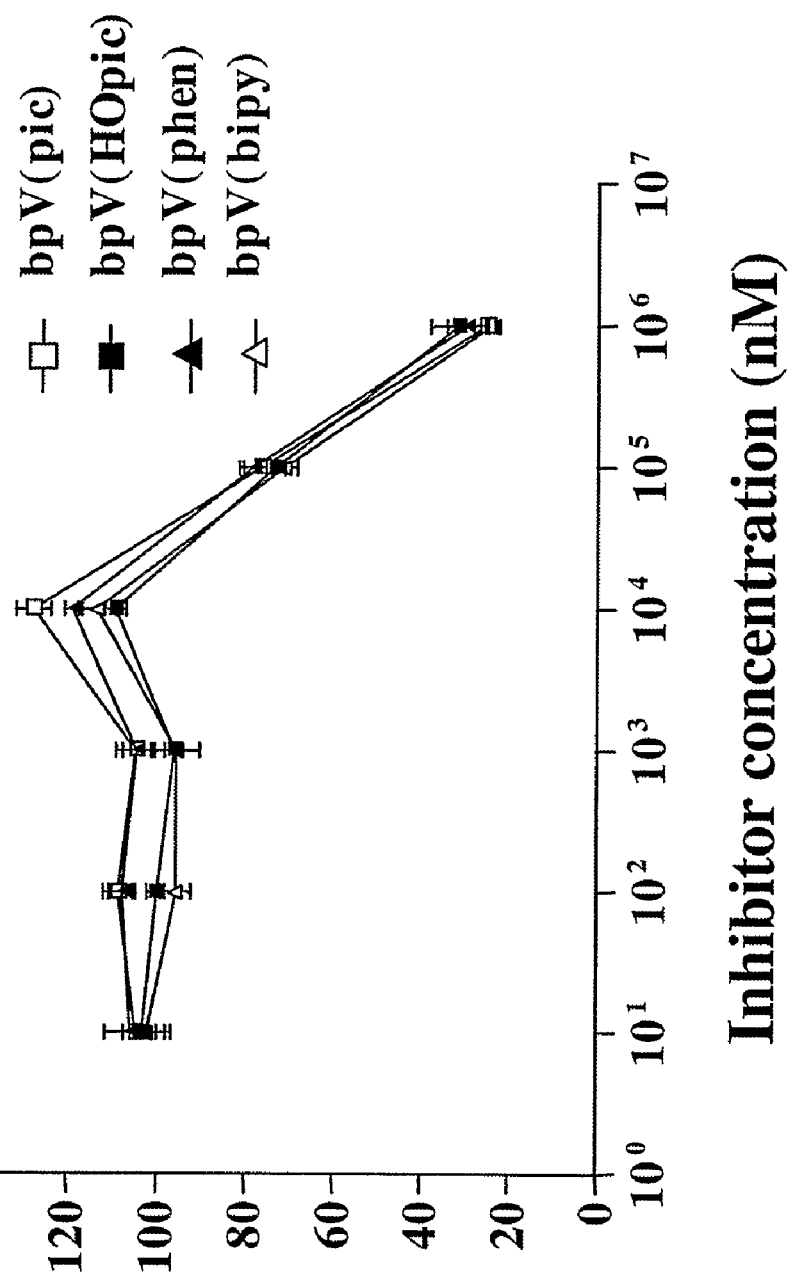

FIG. 2c Cytotoxicity of bpV(pic): NIH3T3 cells were treated with various concentrations of bpV(pic), bpV (HOpic), bpv(bipy) and bpV(phen) and incubated for 2 h. After adding MTT (5 mg/ml) to the cells they were incubated for further 4 h. Finally, OD was measured at 570 nm. Concentrations up to 10 μM had no influence on cell viability, however 100 μM of bpVs affected fibroblasts resulting in about 40% of cell loss. The highest applied dose of 1 mM killed nearly 80% of the cells. The same results were obtained in a second experiment.

Figure 3:
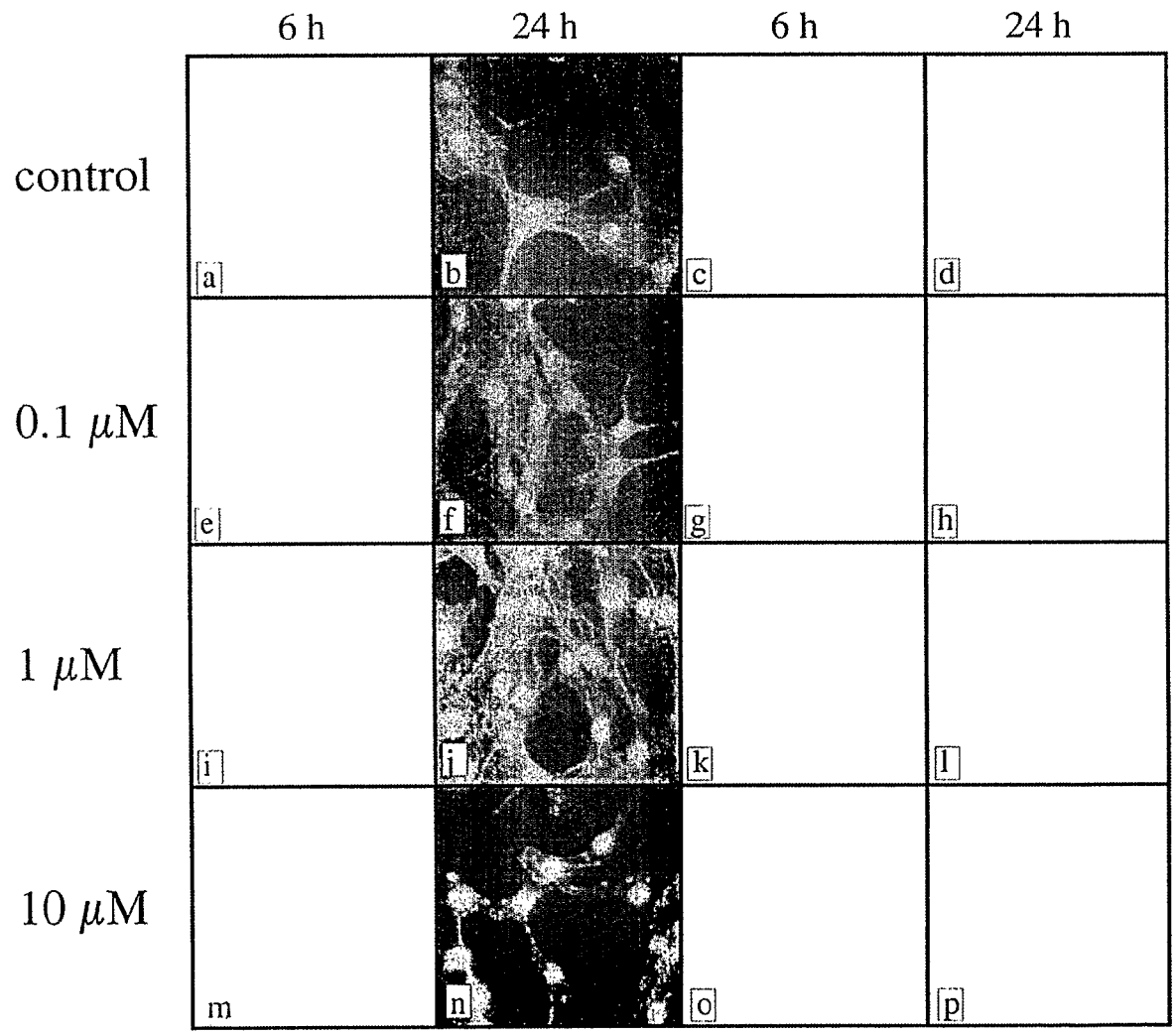

FIG. 3 Actin re-arrangement after bpv(pic) and bpv(phen) incubation: NIH3T3 cells were grown, incubated (0.1-10 μM) and fixed on 8-chamber slides and stained with TRITC-phalloidin and DAPI. Immunofluorescence microscopy was used to analyse the actin staining of the cells. Control cells which were treated only with the vehicle showed the classical actin distribution. After treatment with 0.1 μM of bpV(pic) and bpV(phen) morphology remains unchanged even after 24 h. Only concentrations as high as 1 and 10 μM over 24 h caused morphological changes. Actin filaments started to re-arrange and cells and nuclei round up. Fibroblasts started to detach and die. These findings indicate that toxicity of the compound starts at μmolar concentrations. scale bar=10 μm.

FIG. 4 Effect of μmolar bpV(pic) on PKB phosphorylation in the presence of the PI3K inhibitor Ly294002 and the mTOR inhibitor rapamycin: Resting fibroblasts were pre-incubated with the Ly294002 (10 μM) and rapamycin (50 nM) for 20 min and 30 min, respectively. This was followed by a treatment with either 10 or 1 μM bpV(pic). The PI3K inhibitor ly294002 dimished bpV(pic) induced PKB phosphorylation. In contrast, mTOR inhibitor rapamycin increased phosphorylation level of PKB.

Figure 5A:
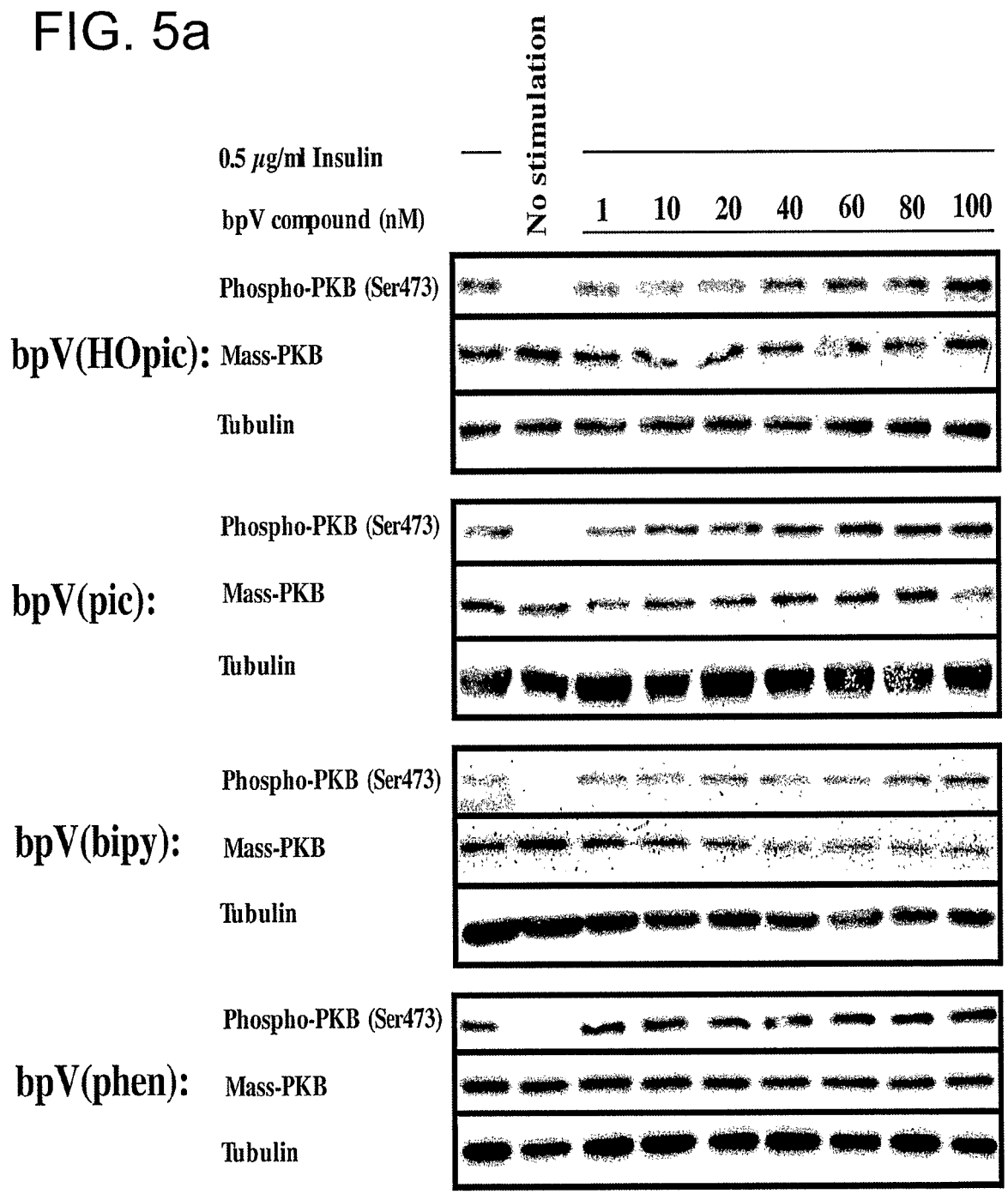

FIG. 5: Dose dependence of PTEN inhibition, in vivo:

FIG. 5a Starved fibroblasts that were incubated with different concentrations of all four bpV compounds for 5 min and stimulated for 15 min with 0.5 μg/ml insulin showed increasing PKB phosphorylation on Western Blots detecting pSer473 in a concentration-dependent manner. Densitometric analysis resulted in in vivo $IC_{50}$ values in the lower nanomolar range using NIH Image program.

Figure 5B:
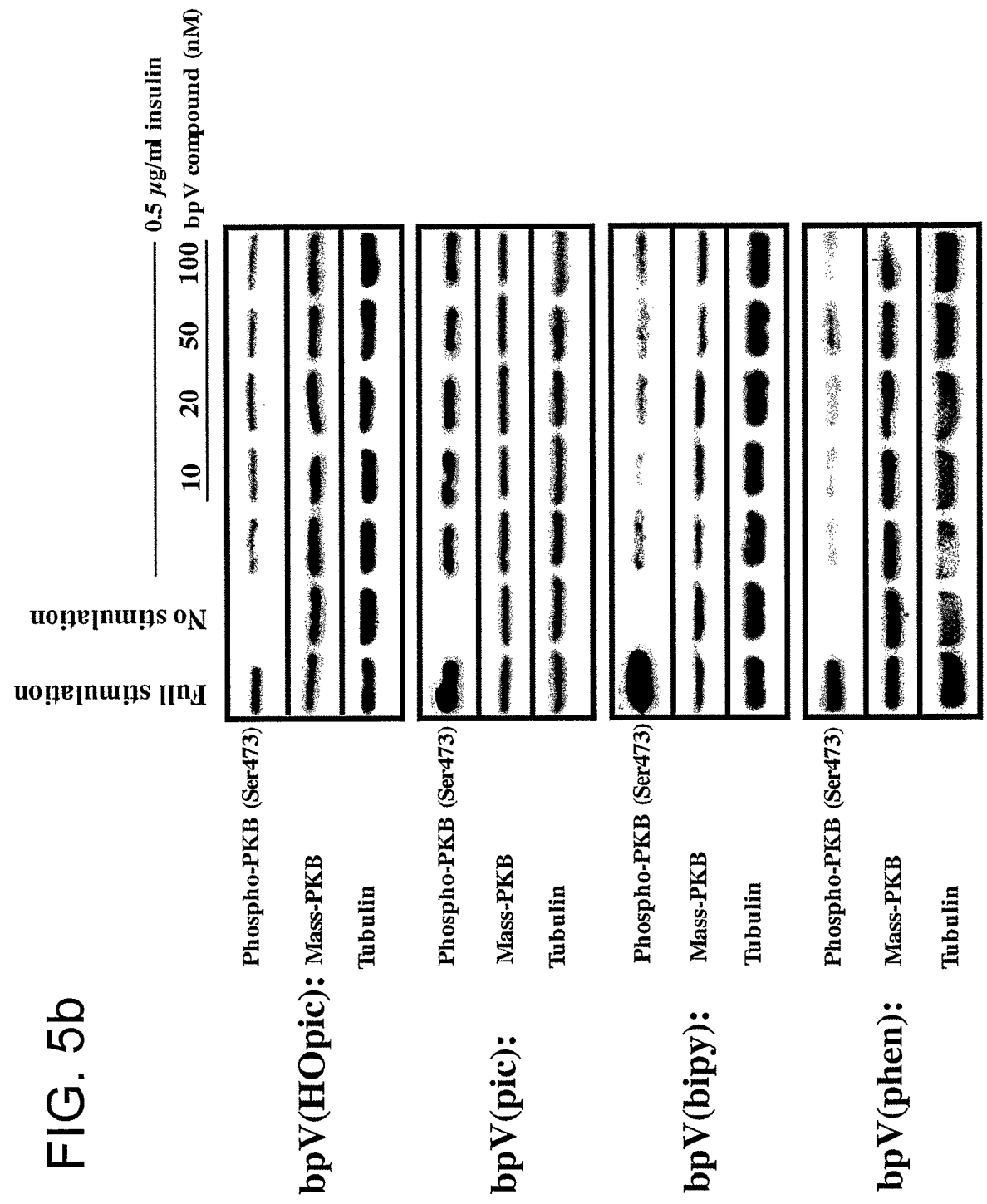

FIG. 5b Similar experiments accomplished in the PTEN-negative cell line UM-UC did not change the phosphorylation level of Ser473 of PKB at the same concentrations indicating that the bpV inhibitors target PTEN. The panel shows results from a representative experiment which were repeated twice.

Figure 6:
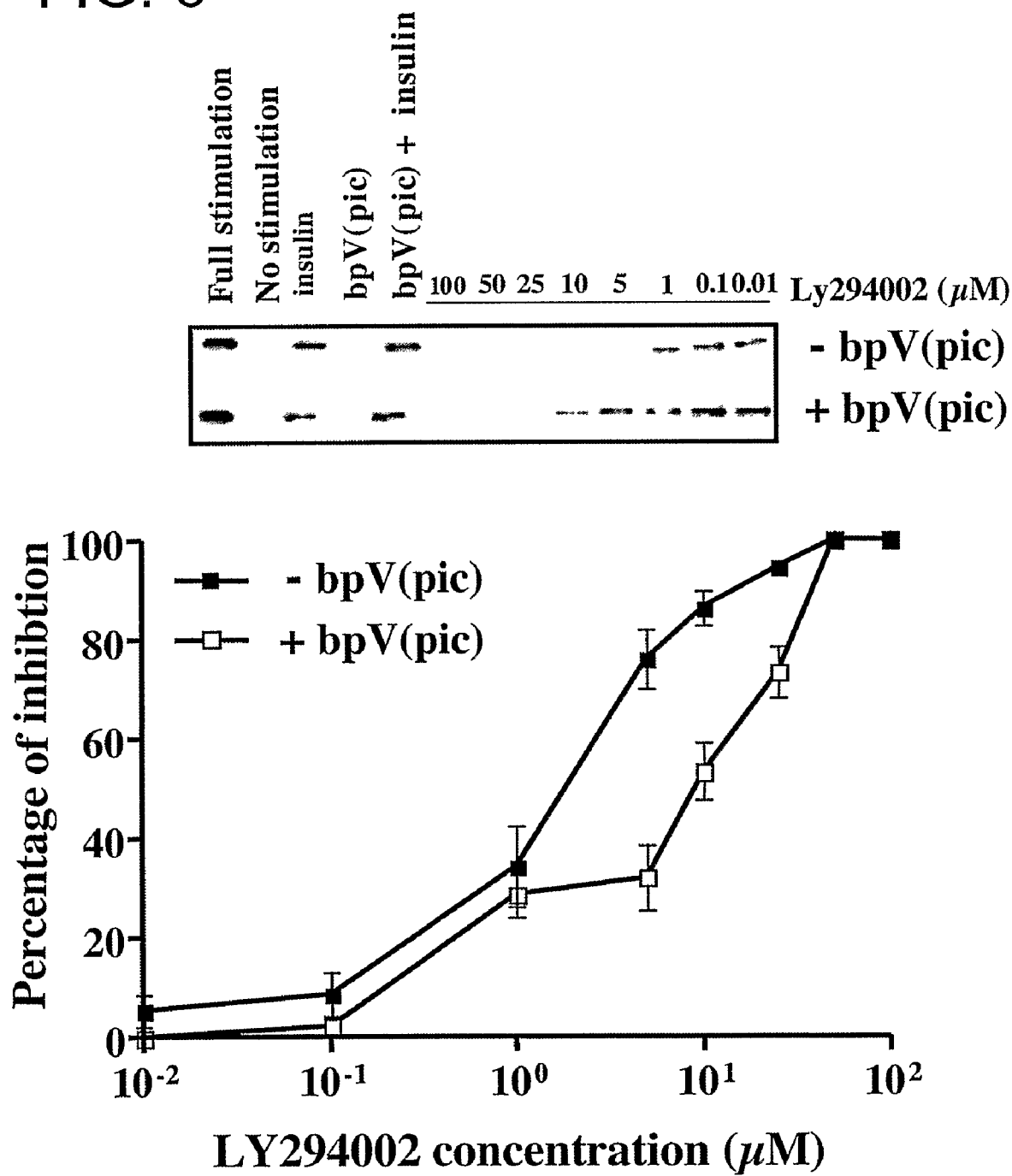

FIG. 6: Dose dependent PKB inhibition by Ly294002 with and without bpV(pic): Experiments were accomplished where Ly294002 pre-treated NIH3T3 cells were incubated with or without 200 nM bpV(pic), followed by a stimulation with 10 μg/ml insulin for 15 min. Cell samples were analysed on PKB Western Blots. Results shown in this figure demonstrate that the PTEN inhibitor bpV(pic) could partly abrogate Ly294002 dependent PKB inhibition. Optical density of bands were analysed using NIH Image and calculated and blottet in PrismGraph. As indicated on the graph 5 μM Ly294002 are sufficient to inhibit PKB activation completely, however in the presence of 200 nM bpV(pic) phosphorylation still occurs. Therefore, the PTEN inhibitor shifts the $IC_{50}$ of Ly294002.

FIG. 7: Summary of characterised features of a new class of PTEN inhibitor: bpVs

EXAMPLE 1

Cloning and Expression of PTEN

The coding region of the DNA sequence of human PTEN was cloned into a pGEX-4T2 expression vector (Pharmacia). Protein expression was induced overnight in the *Escherichia coli* DH5□ strain using 100 μM IPTG at 18 C. GST-fusion proteins were purified according to the manufacturer's manual using glutathione sepharose 4B (Pharmacia). Protein integrity and specificity were confirmed on a Western Blot using GST antibody (Novagen).

Synthesis of bpV(pic)

$K_2[V(=O)(O_2)_2(pic)] \cdot H_2O$ (pic=pyridine-2-caroxylate) was prepared by adding distilled water to $V_2O_5$ (0.69 g, 3.8 mmol) and KOH (0.49 g, 8.8 mmol) to form a yellow-brown suspension. This was followed by addition of $H_2O_2$ (0.5 ml of a 30% w/v) which produced a bright orange solution with some brown precipitate. The brightly colored solution was filtered through a sinter glass filter and allowed to stand for 30 minutes. More $H_2O_2$ (10 ml) was added to the reaction mixture followed by addition of picolinic acid (0.97 g, 7.9 mmol). The solution was stirred for further 30 minutes after which time ethanol (40 ml) was added dropwise precipitating a bright yellow compound. This solution was left standing at 4° C. for two days and all yellow solid produced was collected by filtration, washed 3 times with dry ethanol and dried under reduced pressure overnight (yields vary between 40 and 80% depending on the L-L ligand used). Yield: 1.62 g; 58%. This compound was characterised by NMR and IR spectroscopy and its purity established by elemental analysis. Elemental analyses: Found: C, 19.7; H, 2.0; N, 3.7. Calculated for $C_6H_4NO_7K_2V.2H_2O$: C, 19.6; H, 2.1; N, 3.8. IR ν (KBr): 1630 (CO); 951 (VO), 860, 872 (OO) cm$^{-1}$. $^{51}$V NMR (D$_2$O): −744.1 ppm.

Protein Tyrosine Phosphatase (PTPase) Assay

Protein tyrosine phosphatase (PTPase) assays were performed using the synthetic substrate p-nitrophenylphosphate (pNPP) and the phosphatases PTP-1B and PTP-β (Upstate Biotechnology). The standard assay conditions were 25 mM HEPES pH 7.2, 50 mM NaCl, 5 mM DTT, 2.5 mM EDTA, 100 µg/ml BSA, 1 mM pNPP (Sigma) and 4 unit PTP-1B and 10 unit PTP-β, respectively. The assay was started by adding the enzyme and was carried out for 15 min at 30 C in a preheated ELISA reader chamber. The linear increase of absorbance was monitored every 30 seconds at a wavelength of 410 nm. Inhibition studies were performed in the same assay system containing PTPase inhibitors such as bpV(bipy), bpV(HOpic), and bpV(phen) (Calbiochem) and the synthesised compound bpV(pic) at concentrations between 100 µM and 1 nM.

Malachite Green Phosphate Release Assay and IC$_{50}$ Studies with PTEN

Enzyme activity of recombinant PTEN was measured with a malachite green dye based phosphate release assay (No 230, No 83). The standard assay conditions were 200 mM Tris pH 7.4, 50 ng/µl BSA, and 15 ng/µl PTEN. The synthetic lipid PI(3,4,5)P3dC16 (Cell Signals) was used as a substrate for PTEN. The lipid was dissolved in methanol/H$_2$O and stored at −20 C. Prior to the use in these PIPase experiments, an appropriate amount of lipid was dried down and resuspended in 1% Octylglycoside (Sigma). After 10 min of sonication lipid samples were ready to be added to the enzyme assay. All assays were started by adding the enzyme into the pre-heated buffer solution, containing PI(3,4,5)P3dC16. Linear PIPase reactions were performed at 30 C for 30 min in an incubation chamber. In order to stop the enzyme reaction, 0.7 volume of colour reagent (2.3 mg/ml malachite green in 3.6 M HCl and 17 mM ammonium molybdate) was added to the enzyme solution. The mixture was allowed to develop for 20 min and the absorbance at 625 nm was measured. For all inhibitor studies inhibitor concentrations from 0.1 nM up to 500 nM were pre-incubated with PTEN and the enzyme assays were started by adding 150 µM sonicated lipid. To normalize the phosphate release a phosphate standard curve was used. All experiments were repeated in tripletts. Calculations for IC$_{50}$ values were performed using GraphPad Prism.

Cytotoxicity Assay

Cytotoxicity of bpV compounds was measured doing MTT assays. NIH3T3 cells were resuspended in serum-free media and exposed to concentrations of all four bpV compounds between 1 mM and 0.1 nM for 2 h. MTT solution (5 mg/ml) (Lancaster Synthesis Ltd) was added to the cells and further incubated for 4 h. Cell pellets were resuspended in DMSO containing 100 mM HCl and measured at 570 nm.

Phalloidin Staining

In order to monitor morphological changes NIH3T3 cells were grown on 8-well chamber slides and incubated with concentrations of bpV(pic) and bpV(phen) between 0.1 and 10 µM for 6 h and 24 h, respectively. Fibroblasts were fixed with 4% para-formaldehyde (PFA), permeabilised with 0.2% Triton and blocked with 10% NCS (newborn calf serum). To stain actin filaments cells were incubated with TRITC-phalloidin (Sigma) (1:1000) for 1 h. Finally, nuclei were DAPI (Sigma) stained and mounted. Morphological analyses were assessed on a microscope using filters for TRITC and DAPI and pictures were captured using a camera.

Tissue Culture

NIH3T3 cells (passage 5-20) were grown in 10% NCS D-MEM (GIBCO BRL) in 6-well plates at 37 C and 5% CO$_2$. Starvation of the cells was carried out over 72 h in D-MEM containing 0.5% NCS. Prior use medium was changed to 0% D-MEM. UM-UC-3 cells which is a PTEN$^-$ bladder tumour cell line (NO 195, No 196) were grown in 10% MEM (GIBCO BRL), starved with 0.5% MEM also for three days and finally incubated with serum free MEM.

PKB Assay: Activation of the Insulin Signalling Pathway by bpV Compounds

In order to establish the insulin mimetic property of the four bpV compounds NIH3T3 and UM-UC-3 cells were exposed to bpV(bipy), bpV(phen), bpV(HOpic) and bpv(pic) with concentrations of 0.1, 1 and 10 µM for 15 min. Cells were washed once with PBS and lysed using 80 µl SDS-PAGE buffer (250 mM Tris pH 6.8, 20% glycerol, 4% SDS, 0.01% bromphenol blue, 50 mM mercaptoethanol). Samples were boiled for 15 min and stored at −20 C until analysis on Western Blots as described in the last paragraph.

Phosphotyrosine Assay with NIH3T3 Cells

NIH3T3 cells were grown and starved as described earlier. After 72 h starvation cells were incubated for 15 min with 10% NCS, 50, 10 and 0.5 kg/ml insulin (Sigma), 10, 1, 0.1 and 0.01 µM bpV(pic) and bpV(phen), respectively. Cell lysates were prepared as described above and all samples were analysed on Western Blots using an anti phospho-tyrosine antibody (Upstate).

PKB Assay in the Presence of PI3K Inhibitor Ly294002 and mTOR Inhibitor Rapamycin In order to study the influence of PI3K and mTOR on the bpV-dependent insulin mimetic feature we treated NIH3T3 cells with 10 µM LY294002 (Promega) and 50 nM rapamycin (Calbiochem) for 20 min and 30 min, respectively, followed by an incubation with 10 µM or 1 µM bpv(pic) for 15 min. Cell lysates were analysed on PKB Western Blots.

PKB Assay: Dose Dependence of the Inhibitory Effect of bpV Compounds on PTEN

For studying the inhibitory potency of the vanadate molecules on PTEN bpV(bipy), bpV(HOpic), bpV(pic) and bpV(phen) were added to the cells with concentrations from 1 nM up to 100 nM for 5 min, followed by a stimulation with 0.5 µg/ml insulin for 15 min. UM-UC-3 cells were treated in exactly the same manner. Cell samples were analysed on Western Blots with PKB antibodies.

Ly294002 Dose Dependence

In order to find out whether bpV(pic) has an influence on Ly294002-dependent PKB inhibition we accomplished a dose response experiment applying concentrations from 0.01 up to 100 µM Ly294002 to two sets of quiescent fibroblasts and incubated for 20 min. One batch of cells were then further treated with 200 nM bpV(pic) (5 min) and all cells were finally stimulated with 10 µg/ml insulin for 15 min. Cell lysates were collected as described earlier. Calculations and graph were performed using GraphPad Prism.

Western Blot Analysis

All cell lysate samples were loaded on 10% SDS-PAGE and transferred to PVDF membranes for PKB analysis and nitrocellulose for phospho tyrosine detection. For PKB Western Blots membranes were blocked for 1 h with 5% milk powder in TBST followed by an incubation with anti Mass PKB antibody (1:1000) or anti phospho-PKB (Ser473) antibody (1:1000) in TBST for 2 h. Finally, membranes were exposed to a horseradish peroxidase-conjugated secondary antiserum (BIORAD) (1:1000) in 5% milk powder solution for 1 h. The Western Blots were developed with ECL™ solution (Amersham). In order to detect phosphorylated tyrosine residues nitrocellulose membranes were blocked for 1 h with 2.5% milk powder, first incubated with a specific anti phosphotyrosine antibody (4G10) (1:3000) for 1 h, and finally with horseradish peroxidase-conjugated secondary anti mouse antiserum. All PKB and Phospho-Tyrosine experiments were accomplished in three independent experiments and all membranes were re-probed using a specific tubulin antibody (1:1000). Density analysis of bands took place using the public domain NIH Image V1.62 program (developed at the U.S. National Institutes of Health and available on the Internet at http://rsb.info.nih.gov/nih-image/). Intensity of the pS473 bands were standardised with those of the corresponding Mass PKB and expressed as an arbitrary unit in order to demonstrate changes to controls.

Results $IC_{50}$ for the protein tyrosine phosphatases PTP-1β and PTP-β-PTPase assays were employed using pNPP as a substrate without and in the presence of bpV inhibitors. We demonstrated $IC_{50}$ values for each different compound (Table 1). One can distinguish two groups of bpV compounds, the aromatic (bpV(bipy) and bpV(phen)) and the polar inhibitors (bpV(HOpic) and bpV(pic)). PTP-β assays with the aromatic molecules resulted in $IC_{50}$ values of 60.3 nM (+/−9.6) and 343 nM (+/−88.5), respectively. These results correspond with values published earlier Surprisingly, the $IC_{50}$ for the two polar compounds bpV(HOpic) and bpV(pic) are as high as 4.9 μM (+/−0.9) and 12.7 μM (+/−3.2). Comparable results could be measured for the non-receptor like PTP-1B (for $IC_{50}$ values see FIG. 1).

PTEN is Inhibited by bpV Compounds $IC_{50}$ analysis-PTEN is a 3-phosphatase that shows substrate affinity towards PI(3)P, PI(3,4,5)P3 and IP4. We established a phosphate release assay for the PTEN using PI(3,4,5)P3 as a substrate. This enzyme assay is based on a method which was established many years ago (No 230, No 83). Free inorganic phosphate was detected using an acidic malachite green dye ($OD_{625}$). This assay was established for the phosphoinositol phosphatase PTEN earlier (No 131). The $K_m$ value for PTEN is about 150 μM which corresponds to a mol percentage of 1.72 (data not shown). Furthermore, we could establish for the first time that bpV compounds not only inhibit PTPs but also block phosphoinositol phosphatase activity of PTEN. To further characterise the inhibitory potencies we accomplished $IC_{50}$ studies by incubating an appropriate amount of PTEN with 150 μM PI(3,4,5)P3dC16 and various concentrations of all four bpV compounds. The results of the $IC_{50}$ studies are summarised in FIG. 1. We measured surprisingly low $IC_{50}$s for all four inhibitors resulting in values between 14 and 38 nM. These numbers are 10 to 100 fold lower than those for the PTPases indicating that this class of inhibitors shows much higher affinity to the active site of PTEN. Furthermore, we could not detect a significant difference between the two different groups of bpVs showing that binding of these vanadates in the active centre of PTEN is not affected by the different ligands. These findings characterise a new class of very potent PTEN inhibitors that can be exploited as highly useful tools in pharmalogical studies in the future.

PKB Assays: Activation of the Insulin Signalling Pathway by bpV Compounds

It has been shown in the past that high doses of vanadate, pV and bpV resulted in PKB phosphorylation (No 184, 234). To assess this function of bisperoxo vanadates on the activation of the insulin signalling pathway we incubated starved NIH3T3 and UM-UC-3 cells with concentrations ranging from 0.1 μM up to 10 μM of bpV(pic), bpV(HOpic), bpv(bipy) and bpV(phen). FIG. 2a demonstrates the results revealed on PKB Western Blots using anti pS473 and Mass PKB antibodies. A concentration of 10 μM gave the highest signal for phosphorylated PKB for all compounds in NIH3T3 cells. By using 1 μM we still could detect a weak signal for bpV(pic), bpV(HOpic) and bpV(bipy), however, no phosphorylation was visible for bpV(phen). The lowest concentration (100 nM) did not result in phosphorylation of PKB for any of the pV compounds implying that the insulin mimetic property is detectable only in a μmolar range. Interestingly, bpv(phen) seemed to have lower potency to mimic the insulin pathways than the other molecules. This could be due to different targets in the signalling cascade. No further activation of phosphorylated PKB could be observed after a prolonged incubation time with the bpV molecules (data not shown). In comparison, results revealed in UM-UC-3 cells showed a higher background level of phosphorylated PKB due to the absence of PTEN in this cell line. Apart from that, stimulation of PKB occurred in a similar fashion as described for NIH3T3 cells.

Assessment of the stability of all four inhibitors was performed by pre-incubation of the bpVs for up to 24 h. No differences could be observed (optical density was measured using NIH image) indicating that these molecules are highly stable in our assay conditions (data not shown). The Western Blot analysis for the mass PKB antibody showed consistent signals for all samples indicating a uniform expression level in all cells.

The bpV Inhibitors Increased Phosphorylation of Tyrosine Residues

In order to detect the phosphorylation of tyrosine residues which is one main feature in insulin signalling pathways we incubated quiescent fibroblasts with different concentrations of bpV(pic) and bpV(phen) (10 μM to 0.01 μM), NCS (10%) and insulin (50, 10 and 0.5 μg/ml). The Western Blot analysis for phosphorylated tyrosine residues revealed the typical pattern of protein bands (FIG. 2b) of stimulated cells (No 277, 278,279). The negative control showed a similar pattern however much weaker signals and some bands are absent. The highest degree of tyrosine phosphorylation could be detected in cells treated with 10 μM bpV(pic) which is in correspondence to published data where phosphorylation of tyrosine residues was revealed with 10 μM sodium orthovanadate (No 279), 100 μM vanadate (No 282) or 0.5 mM pervanadate (No 238). These results showed that the highest dose of bpV(pic) is even more potent than 50 μg/ml insulin and 10% NCS. In correspondence to the results demonstrated in the PKB analysis 10 μM bpV(phen) effected lower stimulation than the equivilant concentration of bpV(pic). This gives another evidence that bpv(phen) has a lower insulin mimetic potency than the other compounds. Treatment with 1 and 0.1 μM bpV(pic) resulted in similar signals as revealed after incubation with 0.5 μg/ml insulin. Furthermore, the lowest concentration (0.01 μM) is not distinguishable to the negative control. To summarise these results one can say that bpV compounds show insulin mimetic characteristics only in µmolar concentrations and that there is a remarkable diversity between the aromatic bpV(phen) and the polar bpV(pic) in means of tyrosine phosphorylation.

Cytotoxicity of bpV Compounds

Doing MTT assays, a means of measuring the activity of living cells via mitochondrial dehydrogenases, we clearly showed that concentrations up to 10 µM of all four compounds had no effect on the survival of the fibroblasts (FIG. 2c). Only a concentration as high as 100 µM is significantly cytotoxic killing about 40% of the cells. Treatment with 1 mM of the inhibitors led to the death of about 80% of the cells. This indicated that doses which can inhibit PTEN phosphatase activity in vitro do not affect cell viability. No difference in cytotoxicity could be observed between the four compounds.

Morphological changes after inhibitor exposure represented by actin re-arrangement NIH3T3 cells immuno stained with Phalloidin-TRITC and DAPI showed the cytoskeletal morphology of the fibroblasts. Actin staining of fibroblasts is a well-established techniques (No 280, No 281). The occurrence and distribution of actin stress fibers can be a mass of integrity of cells (No 283, No 266, No 271) and in turn cytotoxicity of drugs can be measured as a mean of actin arrangement. Control cells treated only with the vehicle displayed the classic cytoskeleton actin structure and the occurrence of stress fibers (FIGS. 3a-d). After treatment with 0.1 µM of bpV(pic) and bpV(phen) for 6 h and 24 h cellular morphology remained unchanged (FIGS. 3e-h). Only incubation with concentrations as high as 1 and 10 µM over 24 h revealed altered morphology characterised by the loss of actin stress fibers and the presence of thick areas of F-actin at the edges of affected cells (FIGS. 3kj,l,n+p). Fibroblasts started to detach and die. Furthermore, cells and nucleus rounded up which are typical features of dying cells. Fibroblasts exposed to 1 and 10 µM bpVs only for 6 h showed similar actin distribution and morphology as it could be seen in the control cells. These findings indicate that toxicity of the compound starts at µmolar concentrations. Furthermore, no significant differences could be observed within the two groups of bpV compounds giving evidence that in terms of cytotixicity there exist no diversity between polar and aromatic bpV vanadates.

Influence of Ly294002 and rapamycin on bp vanadate induced insulin pathway Ly294002 is a well-known PI3-K inhibitor that blocks phosphorylation of PKB. In contrast, rapamycin inhibits mTOR, the so-calles mammalian target of rapamycin. We investigated the influence of these two inhibitors on the bp vanadate induced insulin pathway. NIH3T3 cells were pre-incubated to an appropriate dose of Ly294002 and rapamycin and then exposed to 10 and 1 µM bpV(pic), respectively. As demonstrated earlier starved, non-stimulated fibroblasts need µmolar concentrations of bpVs to induce phosphorylation of Ser473 of PKB (FIG. 2a). As shown in FIG. 4, 10 µM bpV(pic) resulted in a high degree of phosphorylation. Addition of 50 nM rapamycin gave a similar stimulation, however pre-incubation with Ly294002 effected reduced phosphorylation rate. This proves that the phosphorylation of PKB by the vanadates is a PI3-K dependent pathway. Additionally, we could show that at a concentration of 1 µM bpV(pic) (longer exposure time FIG. 4) no signal was visible, nevertheless pre-incubation with rapamycin provoked phosphorylated Ser473 implicating a role for mTOR in this signalling pathway.

bpV Compounds Stimulated PKB Phosphorylation at Nanomolar Concentrations

Investigating the potency of bpV inhibitors we performed concentration dependent experiments with all four compounds. Quiescent NIH3T3 cells were incubated with concentrations of 1 nM up to 100 nM of bpV(HOpic), bpV(pic), bpV(bipy) and bpV(phen). The compounds induced the phosphorylation of PKB in a dose-dependent manner (FIG. 5a). No activation could be established with the lowest concentrations such as 1 and 10 nM, however, a slight increase could be detected with 20 nM bpV(pic), bpV(HOpic) and bpV (bipy) (about 20%) in comparison with the control (0.5 µg/ml insulin). Higher concentrations such as 60 nM to 100 nM resulted in a significant enhancement of the phosphorylated PKB signal. Optical density was measured using NIH Image program and $IC_{50}$ values could be calculated in relation to the results of three independent experiment. These inhibition coefficients could be established between 48 nM (+/−8.5) for bpV(pic) and 96 nM (+/−16.3) for bpV(HOpic). To summarise these results, one can say that PTEN can also be inhibited with lower nanomolar concentrations of bpV compounds in vivo, as established in vitro (FIG. 1). Thus, the stimulation of PKB is due to increased intracellular PI(3,4, 5)3 levels provoked by PTEN inhibition. Furthermore, we could not detect any diversity between the two groups of inhibitors indicating that the active site of the PTEN phosphatase does not limit access in terms of size or charge. By establishing this distinct difference of inhibition in respect of PTPs and PTEN these molecules can be explored as useful tools to distinguish between various classes of phosphatases.

bpVs Showed no Effect on PKB Phosphorylation in UM-UC-3 Cells

To further prove the fact that bpVs inhibit PTEN and thus effect higher PI(3,4,5)P3 levels which leads to PKB phosphorylation we repeated the same experiments in the PTEN negative tumour cell line UM-UC-3. Starved UM-UC-3 cells were exposed to similar concentrations of all four inhibitors. The analysis of pS473 Western Blots did not show any stimulation of PKB (FIG. 5b). Even the highest dose of 100 nM bpV inhibitors only increased the phosphorylation slightly implying that there occurred a shift of $IC_{50}$ for the bpVs. These results indicated once more that PTEN and subsequently PI(3,4,5)3 are the key molecules in the activation of PKB induced by bpV compounds in our cell system.

PTEN Inhibitor bpv(pic) can Partly Abrogate Ly294002 Induced PKB Inhibition

Quiescent NIH3T3 cells that were pre-incubated with various concentrations of Ly294002 (0.01 to 100 µM) alone gave significantly lower signals on pSer473 Western Blots than those which were co-treated with 200 nM bpV(pic). This shift in $IC_{50}$ clearly demonstrated that bpV(pic) can abrogate Ly294002 induced PKB inhibition. The analysis of the optical density of the Western Blot signals were standardised to the control and calculated to means of inhibition. The graph shown in FIG. 6 demonstrates significant differences for the experiments with and without bpV(pic). The presence of the bpV compounds effects a reduction of Ly294002 induced inhibition. These results give clear evidence that in our cell system bpVs act as PTEN inhibitors and subsequently increased PI(3,4,5)P3 levels resulted in phosphorylation of PKB.

The Following Six Compounds were Tested as Inhibitors of Inositol Phosphatases

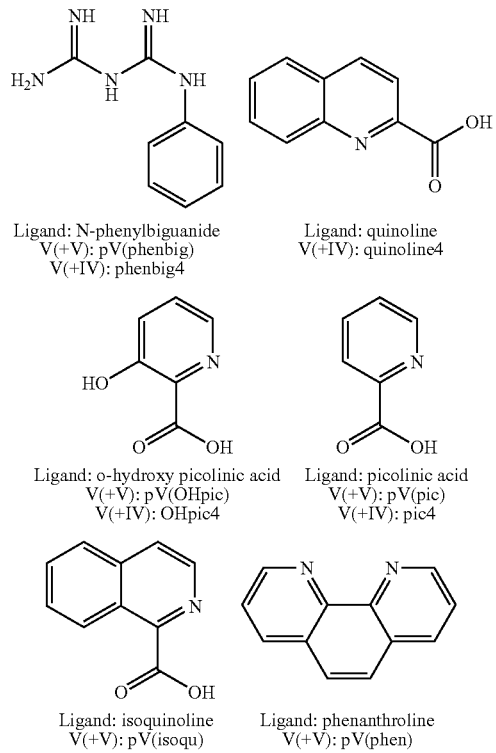

Ligand: N-phenylbiguanide
V(+V): pV(phenbig)
V(+IV): phenbig4

Ligand: quinoline
V(+IV): quinoline4

Ligand: o-hydroxy picolinic acid
V(+V): pV(OHpic)
V(+IV): OHpic4

Ligand: picolinic acid
V(+V): pV(pic)
V(+IV): pic4

Ligand: isoquinoline
V(+V): pV(isoqu)

Ligand: phenanthroline
V(+V): pV(phen)

summary of compounds tested in this study;
pV = peroxovanadate; Vanadium (+V) complexes VO(O$_2$)$_2$ (ligand);
Vanadium (+IV) complexes VO (ligand)$_2$

PTP-beta

| V(+V) | IC$_{50}$ PTPβ | V(+IV) | IC$_{50}$ PTPβ |
|---|---|---|---|
| pV(phen) | 240 ± 8.3 nM$_{MM}$ | — | — |
| pV(isoqu) | 349 ± 26.5 μM$_{MM}$ | — | — |
| — | — | quinoline 4 | 212 ± 9.4 μM |
| pV(phenbig) | 640 ± 32.1 μM | phenbig 4 | 112 ± 4.9 μM |
|  | (834.9 ± 34.7 μM)$_{MM}$ |  |  |
| pV(pic) | 4.9 ± 0.9 μM$_{MM}$ | pic 4 | 589 ± 32.9 μM |
| pV(OHpic) | 12.7 ± 3.2 μM$_{MM}$ | OHpic 4 | 57.5 ± 9.4 μM | pV(phen) > pV(pic) > pV(OHpic) > OHpic4 > phenbig4 > quinolin4 > pV(isoqu) > pic4 > pV(phenbig)

SopB

| +V compound | IC$_{50}$ SopB | +IV compound | IC$_{50}$ SopB |
|---|---|---|---|
| pV(phen) | 102 nM* | — | — |
| pV(isoqu) | 79.8 ± 9.7 nM | — | — |
| pV(pic) | NA | pic4 | 125 ± 1.65 nM |
| pV(OHpic) | 33.2 ± 6.5 nM | OHpic4 | 588 ± 163.1 nM |
| pV(phenbig) | 798 ± 41.0 nM | phenbig4 | 811 ± 88.25 nM |
| — | — | quinolin4 | 1.96 ± 0.87 μM | pV(OHpic) > pV(isoqu) > pic4 > OHpic4 > pV(phenbig) > phenbig4 > quinolin4

MTM

| Compound(+V) | MTM IC$_{50}$ | Compound(+IV) | MTM IC$_{50}$ |
|---|---|---|---|
| pV(phen) | 407.3 ± 38.5 nM | — | — |
| pV(isoqu) | 868 ± 186.6 nM | — | — |
| pV(pic) | 239 ± 4.2 nM | Pic4 | 6.35 ± 3.92 μM |
| pV(OHpic) | 346 ± 24.8 nM | OHpic4 | 4.03 ± 0.04 μM |
| pV(phenbig) | 1.89 ± 0.83 μM | Phenbig4 | 4.37 ± 0.94 μM |
| — | — | Quinolin4 | 9.26 ± 0.04 μM | pV(pic) < pV(OHpic) < pV(phen) < pVisoqu) < pV(phenbig) < OHpic4 < phenbig4 < pic4 < quinolin4

PTEN

| compound | Malachite green endpoint assay | | Preliminary data (western blots) | Published data In vitro enzyme assay confirmed by in vivo data |
|---|---|---|---|---|
| | PTEN inhibition with 100 nM compound | PTEN inhibition with 1 μM compound | | |
| pV(pic) | 26.7% | 16.3% | NA | 31 ± 1.7 nM |
| pV(phen) | NA | NA | 275 nM | 38 ± 2.4 nM |
| pV(isoqu) | NA | NA | 101.4 nM | NA |
| pV(phenbig) | 12.2% | 9.2% | 48.5 nM | NA |
| pV(OHpic) | 54.8% | 47.4% | 211.3 nM | 14 ± 2.3 nM |
| Pic4 | 30.1% | 0.0 | NA | NA |
| OHpic4 | 8.1% | 3.3% | NA | NA |
| Phenbig4 | 60.2% | 45.4% | NA | NA |
| Quinoline4 | 56.6% | 39.8% | NA | NA |

All compounds seem to inhibit in low nM range;
pV(phenbig) and OHpic4 seem to be very good inhibitors.

Discussion

For many years, PTEN has been described as a tumour suppressor being mutated in many cancer tissues (No 240, 246, 247, 267). It is now established that its role as a tumour suppressor is mainly exerted by the negative regulation of the PI3K/PKB signalling pathways (No, 236, 232, 265). Even though many recent studies are characterising PTEN as a phosphatase (see review No 98) and its role in metabolism and disease (No 267, 268, 246, 247) there exist no-specific inhibitors for this protein. Studies are mainly accomplished in PTEN null cell lines (No 106, 164, 233, 236) or in a PTEN negative Drosophila mutant (No 175). The work presented here is the first study describing a very potent class of PTEN inhibitors. We could demonstrate that the well-known protein tyrosine phosphatase (PTPase) inhibitor class of bisperoxovanadiums (bpVs) show very high affinity towards PTEN. We characterised these compounds in vitro and in vivo and detected remarkable differences compared to the PTPase inhibitory properties. These insulin mimetics initiate pathways which are activated after growth factor stimulation of cells. Their features are mainly exhibited by inhibiting PTPases which dephosphorylates target protein such as insulin receptor substrate IRS-1. In order to assess these insulin mimetic features of bpVs in our cell system we applied μmolar doses to fibroblasts and analysed phosphorylation degree of the Ser473 residue of PKB (FIG. 2a) and tyrosine residues (FIG. 2b). In correspondence to the literature (No 140) we demonstrated increased level of phosphorylation in both cases.

In PTPase assays we revealed a clear difference between the polar (bpV(HOpic) and bpV(pic)) and the aromatic (bpV(phen) and bpV(bipy)) bpVs. The latter resulted in higher nanomolar IC$_{50}$ values, however the polar compounds effected 50% inhibition at concentrations as high as µmolar (FIG. 1). Variations to published data might be due to assay conditions. It has been described that IC$_{50}$ values may depend on buffer conditions such as DTT and EDTA concentration (No 146, 206). To analyse PTEN activity we performed phosphate release assays using an acidic malachite green dye (No 230, No 83). This assay has been successfully applied for PTEN (No 131) and gives linear results between 1 and 10 nmol of free inorganic phosphate (No 231). In the same study it was shown that this method is appropriate to investigate phosphatase activity in the presence of various inhibitors. Remarkably, inhibitory studies applying all bpVs revealed PTEN inhibition already at low nanomolar concentration. This proves higher affinity of the bpVs towards PTEN. Furthermore, there was no significant difference detectable between the polar and the aromatic compounds as observed for the PTPases. This might be due to the more open structure of the active site of PTEN (No 165), whereby in clear contrast to that PTPases contain a closer structure (No Sonnenberg et al, 2003, Liu et al, 2003). Based on these in vitro data, we performed in vivo studies using quiescent fibroblast that were treated with different concentrations of bpVs and stimulated with insulin. It was recently shown, that starved fibroblast need to be stimulated with a certain dose of growth factors in order to detect drug dependent changes in PKB phosphorylation (Byrne et al). Since PTEN inhibitors lead to the loss of PTEN activity and thus to increased PI(3,4,5)P3 levels, we expected a dose-dependent activation of PKB after treatment with vanadates. We clearly could demonstrate an increase of phosphorylated Ser473 in corelation with nanomolar bpV exposure of the cells (FIG. 5a). Using densitometric analysis we established an inhibition of 50% between 48 and 99 nM for the different compounds. Those values are comparable to the results we received in our enzyme assays. The slight variation to the in vitro results might be due to retarded membrane permeability of the vanadates. Since it is published that insulin and vanadate also activate PKB (No 184, 234), however, in higher concentrations than applied here, we repeated the same experiments in the PTEN negative UM-UC-3 cell line. As proposed, bpVs did not provoke PKB activation indicating that these compounds target PTEN (FIG. 5b). Finally, to further confirm our findings we investigated the influence of the PI3K inhibitor Ly294002 in our cell system. If bpVs act via a PI3K-dependent pathway, one would expect that these compounds could rescue Ly294002 induced PKB inhibition. The application of an appropriate concentration of Ly294002 prevented PKB phosphorylation (FIG. 6). However, co-treatment with bpV(pic) could abrogate this inhibition which clearly demonstrates that bpVs target PTEN which in turn leads to increased PI(3,4,5)P3 levels and to the activation of PI3K/PKB downstream pathways.

REFERENCES

1 Posner, B. I., Faure, R., Burgess, J. W., Bevan, A. P., Lachance, D., Zhang-Sun, G., Fantus, I. G., Ng, J. B., Hall, D. A., Lum, B. S. and et al. (1994) Peroxovanadium compounds. A new class of potent phosphotyrosine phosphatase inhibitors which are insulin mimetics. J Biol Chem 269, 4596-604

2 Cuncic, C., Detich, N., Ethier, D., Tracey, A. S., Gresser, M. J. and Ramachandran, C. (1999) Vanadate inhibition of protein tyrosine phosphatases in Jurkat cells: modulation by redox state. J Biol Inorg Chem 4, 354-9

3 Huyer, G., Liu, S., Kelly, J., Moffat, J., Payette, P., Kennedy, B., Tsaprailis, G., Gresser, M. J. and Ramachandran, C. (1997) Mechanism of inhibition of protein-tyrosine phosphatases by vanadate and pervanadate. J Biol Chem 272, 843-51

4 Rumora, L., Shaver, A., Zanic-Grubisic, T. and Maysinger, D. (2001) Differential regulation of JNK activation and MKP-1 expression by peroxovanadium complexes. Neurochem Int 38, 341-7

5 Shisheva, A. and Shechter, Y. (1993) Mechanism of pervanadate stimulation and potentiation of insulin-activated glucose transport in rat adipocytes: dissociation from vanadate effect. Endocrinology 133, 1562-8

6 Wilden, P. A. and Broadway, D. (1995) Combination of insulinomimetic agents H2O2 and vanadate enhances insulin receptor mediated tyrosine phosphorylation of IRS-1 leading to IRS-1 association with the phosphatidylinositol 3-kinase. J Cell Biochem 58, 279-91

7 Band, C. J., Posner, B. I., Dumas, V. and Contreres, J. O. (1997) Early signaling events triggered by peroxovanadium [bpV(phen)] are insulin receptor kinase (IRK)-dependent: specificity of inhibition of IRK-associated protein tyrosine phosphatase(s) by bpV(phen). Mol Endocrinol 11, 1899-910

8 Shechter, Y. (1990) Insulin-mimetic effects of vanadate. Possible implications for future treatment of diabetes. Diabetes 39, 1-5

9 Maehama, T. and Dixon, J. E. (1998) The tumor suppressor, PTEN/MMAC1, dephosphorylates the lipid second messenger, phosphatidylinositol 3,4,5-trisphosphate. J Biol Chem 273, 13375-8

10 Li, J., Yen, C., Liaw, D., Podsypanina, K., Bose, S., Wang, S. I., Puc, J., Miliaresis, C., Rodgers, L., McCombie, R., Bigner, S. H., Giovanella, B. C., Ittmann, M., Tycko, B., Hibshoosh, H., Wigler, M. H. and Parsons, R. (1997) PTEN, a putative protein tyrosine phosphatase gene mutated in human brain, breast, and prostate cancer. Science 275, 1943-7

11 Steck, P. A., Pershouse, M. A., Jasser, S. A., Yung, W. K., Lin, H., Ligon, A. H., Langford, L. A., Baumgard, M. L., Hattier, T., Davis, T., Frye, C., Hu, R., Swedlund, B., Teng, D. H. and Tavtigian, S. V. (1997) Identification of a candidate tumour suppressor gene, MMAC1, at chromosome 10q23.3 that is mutated in multiple advanced cancers. Nat Genet 15, 356-62

12 Waite, K. A. and Eng, C. (2002) Protean PTEN: form and function. Am J Hum Genet 70, 829-44

13 Downward, J. (1998) Mechanisms and consequences of activation of protein kinase B/Akt. Curr Opin Cell Biol 10, 262-7

14 Stephens, L. R., Jackson, T. R. and Hawkins, P. T. (1993) Agonist-stimulated synthesis of phosphatidylinositol(3,4,5)-trisphosphate: a new intracellular signalling system? Biochim Biophys Acta 1179, 27-75

15 Stocker, H., Andjelkovic, M., Oldham, S., Laffargue, M., Wymann, M. P., Hemmings, B. A. and Hafen, E. (2002) Living with lethal PIP3 levels: viability of flies lacking PTEN restored by a PH domain mutation in Akt/PKB. Science 295, 2088-91

16 Hill, M. M. and Hemmings, B. A. (2002) Inhibition of protein kinase B/Akt implications for cancer therapy.

The invention claimed is:

1. A compound of the formula:

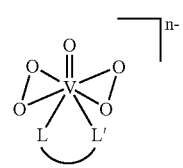

wherein:

L-L' is selected from the group consisting of:

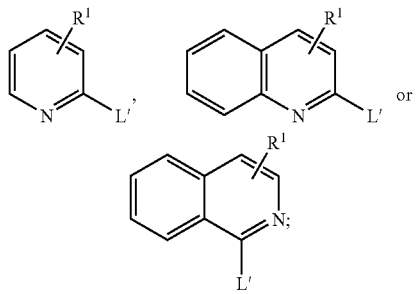

L' is selected from the group consisting of CONR$^5$ and CONHR$^6$;

or L and L' together form the group:

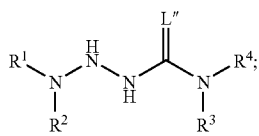

Wherein L" is O, S, or NH,

R$^1$, R$^2$, R$^3$, R$^4$, R$^5$ and R$^6$ are each independently selected from the group consisting of H, hydroxyl, C1-C6 alkyl optionally substituted by hydroxyl or NR$^7$R$^8$, C3-C6 cycloalkyl optionally substituted by hydroxyl or NR$^7$R$^8$, phenyl optionally substituted by C1-C3 alkyl, hydroxyl, NR$^7$R$^8$ or SO$_3$, (OCH$_2$CH$_2$)$_n$(NHCH$_2$CH$_2$)$_n$, an amino acid or a peptide consisting of 2 to 5 amino acids;

R$^7$ and R$^8$ are independently H or C1-C6 alkyl, and n is an integer;

or a pharmaceutically acceptable salt thereof.

2. A compound of the formula:

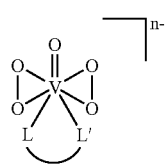

wherein:

L-L' is selected from the group consisting of:

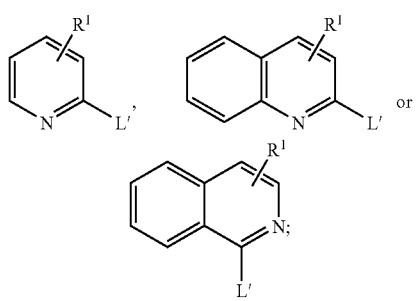

L' is selected from the group consisting of CONR$^5$ and CONHR$^6$;

or wherein L and L' together form the group:

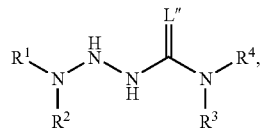

wherein L" is O, S, or NH,

R$^1$, R$^2$, R$^3$, R$^4$, R$^5$ and R$^6$ are each independently selected from the group consisting of H, hydroxyl, C1-C6 alkyl, C3-C6 cycloalkyl and phenyl;

R$^7$ and R$^8$ are independently H or C1-C6 alkyl;

and n is an integer;

or a pharmaceutically acceptable salt thereof.

3. The compound of claim 2 wherein R$^1$, R$^2$, R$^3$, R$^4$, R$^5$ and R$^6$ are each independently selected from the group consisting of H and hydroxyl.

4. A pharmaceutical composition comprising a compound of claim 1 and pharmaceutically acceptable carrier or excipient.

5. A method of inhibiting an inositol phosphatase in a patient in need thereof comprising administering to said patient therapeutically effective amount of a compound of the formula:

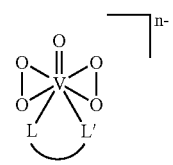

wherein:

L-L' is selected from the group consisting of:

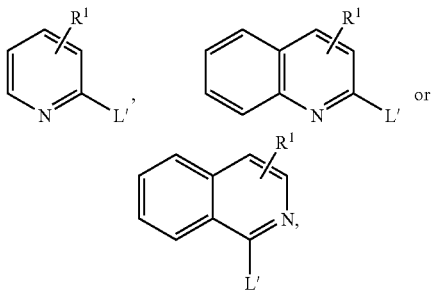

L' is selected from the group consisting of CONR$^5$, CONHR$^6$ and CH$_2$NR$^5$R$^6$, or wherein L and L' together form a group selected from the group consisting:

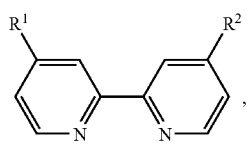

-continued

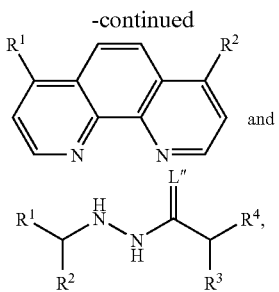
and wherein L" is O, S or NH;

$R^1$, $R^2$, $R^3$, $R^4$ $R^5$ and $R^6$ are each independently selected from the group consisting of H, hydroxyl, C1-C6 alkyl optionally substituted by hydroxyl or $NR^7R^8$, C3-C6 cycloalkyl optionally substituted by hydroxyl or $NR^7R^8$, phenyl optionally substituted by C1-C3 alkyl, hydroxyl, $NR^7R^8$ or $SO_3$, $(OCH_2CH_2)_n(NHCH_2CH_2)_n$, an amino acid or a peptide consisting of 2 to 5 amino acids;

$R^7$ and $R^8$ are independently H or C1-C6 alkyl;

and n is an integer;

or a pharmaceutically acceptable salt thereof.

6. A method of inhibiting an inositol phosphatase in a patient in need thereof comprising administering to said patient therapeutically effective amount of a compound of the formula:

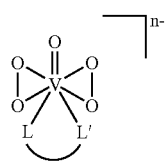

wherein:
L-L' is selected from the group consisting of:

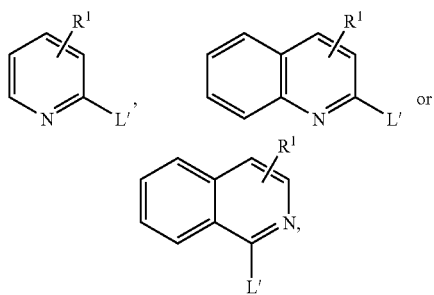

L' is selected from the group consisting of $CONR^5$, $CONHR^6$ and $CH_2NR^5R^6$, or wherein L and L' together form a group selected from the group consisting:

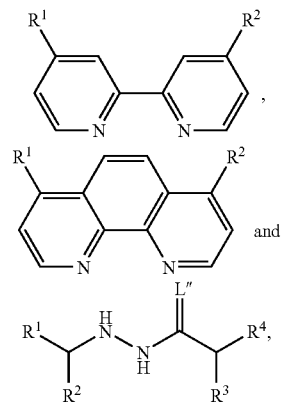

wherein L" is O, S or NH;

$R^1$, $R^2$, $R^3$, $R^4$ $R^5$ and $R^6$ are each independently selected from the group consisting of H, hydroxyl, C1-C6 alkyl, C3-C6 cycloalkyl and phenyl;

$R^7$ and $R^8$ are independently H or C1-C6 alkyl;

and n is an integer;

or a pharmaceutically acceptable salt thereof.

7. The method of claim 6 wherein $R^1$, $R^2$, $R^3$, $R^4$ $R^5$ and $R^6$ are each independently selected from the group consisting of H and hydroxyl.

8. The method of claim 5 wherein the inositol phosphatase is PTEN.

9. The method of claim 5 wherein said patient is suffering from a disease or condition which would benefit from inhibition of apoptosis.

10. The method of claim 5 wherein the disease or condition is selected from the group consisting of wound healing, burns, heart hypertrophy, hypoxia, ischemia, diabetes, sports injuries and cancer.

11. The method of claim 5 wherein the disease or condition is a neurodegenerative disease.

12. The method of claim 5 wherein the neurodegenerative disease is Alzheimer's disease.

13. The method of claim 5 wherein the compound is selected from the group consisting of potassium bisperoxo (bipyridine)oxovanadate, potassium bisperoxo(1,10-phenanthroline)oxovanadate, potassium bisperoxo(picolinate)oxovanadate and potassium bisperoxo(phenylbiguanide) oxovanadate.

14. The method of claim 5 wherein the compound is selected from the group consisting of [dipotassium bisperoxo (phenylbiguanide)oxovanadate] and [dipotassium bisperoxo (5-hydroxypyridine-2-carboxyl)oxovanadate].

15. The method of claim 14 wherein the patient is suffering from diabetes.

* * * * *

UNITED STATES PATENT AND TRADEMARK OFFICE
CERTIFICATE OF CORRECTION

PATENT NO.      : 7,692,012 B2
APPLICATION NO. : 10/581000
DATED           : April 6, 2010
INVENTOR(S)     : Rudiger Woscholski, Erika Rosivatz and Ramon Vilar Page 1 of 1

It is certified that error appears in the above-identified patent and that said Letters Patent is hereby corrected as shown below:

Column 24, Claim 5, Line 45: Please delete "or" and replace with --and--;

Column 25, Claim 5, Line 10: Please delete " 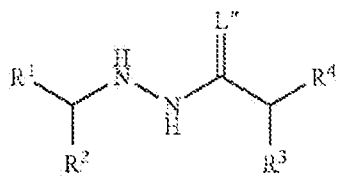 " and replace with -- 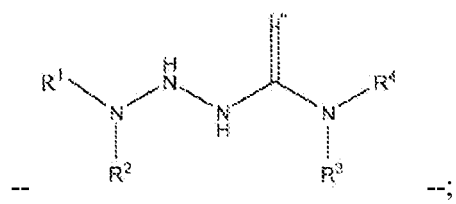 --;

Column 25, Claim 6, Line 45: Please delete "or" and replace with --and--;

Column 26, Claim 6, Line 15: Please delete " 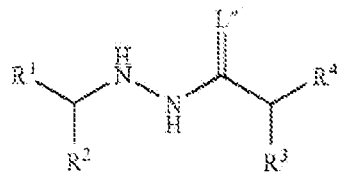 " and replace with -- 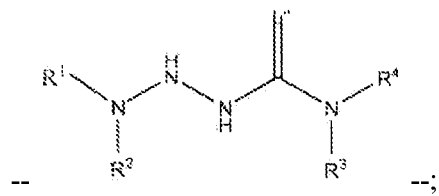 --;

Column 26, Claim 12, Line 42: After "claim" please delete "5" and replace with --11--.

Signed and Sealed this
Twenty-fourth Day of April, 2012

David J. Kappos
*Director of the United States Patent and Trademark Office*